US012806011B2

(12) United States Patent
Guan et al.

(10) Patent No.: US 12,806,011 B2
(45) Date of Patent: Nov. 24, 2026

(54) HEART VALVE PROSTHESES WITH SENSOR FOR HEMODYNAMIC MONITORING

(71) Applicant: Medtronic, Inc., Minneapolis, MN (US)

(72) Inventors: Zeyi Guan, Santa Rosa, CA (US); Geoffrey Orth, Sebastopol, CA (US)

(73) Assignee: Medtronic, Inc., Minneapolis, MN (US)

( * ) Notice: Subject to any disclaimer, the term of this patent is extended or adjusted under 35 U.S.C. 154(b) by 346 days.

(21) Appl. No.: 18/595,751

(22) Filed: Mar. 5, 2024

(65) Prior Publication Data

US 2024/0415639 A1 Dec. 19, 2024

Related U.S. Application Data

(60) Provisional application No. 63/508,069, filed on Jun. 14, 2023.

(51) Int. Cl.
*A61F 2/24* (2006.01)

(52) U.S. Cl.
CPC ........ *A61F 2/2418* (2013.01); *A61F 2210/00* (2013.01); *A61F 2220/0075* (2013.01); *A61F 2250/0002* (2013.01); *A61F 2250/0058* (2013.01)

(58) Field of Classification Search
CPC ........ A61F 2/24; A61F 2/2409; A61F 2/2418; A61F 2002/4666; A61F 2250/0002; A61B 5/6862; A61B 5/02; A61B 5/021; A61B 5/02028; A61B 5/026; A61B 5/02158; A61B 2562/0247; A61B 2017/00022; A61B 5/0031; A61B 5/02007
See application file for complete search history.

(56) References Cited

U.S. PATENT DOCUMENTS

| | | | |
|---|---|---|---|
| 5,967,986 | A | 10/1999 | Cimochowski et al. |
| 5,967,989 | A | 10/1999 | Cimochowski et al. |
| 6,053,891 | A | 4/2000 | Decampli |
| 6,078,832 | A | 6/2000 | Lenker et al. |
| 6,159,156 | A | 12/2000 | Van Bockel |
| 6,206,835 | B1 | 3/2001 | Spillman et al. |
| 6,231,516 | B1 | 5/2001 | Keilman et al. |
| 6,237,398 | B1 | 5/2001 | Porat et al. |
| 6,330,885 | B1 | 12/2001 | Weissman et al. |
| 6,398,734 | B1 | 6/2002 | Cimochowski et al. |
| 6,475,170 | B1 | 11/2002 | Doron et al. |

(Continued)

OTHER PUBLICATIONS

Written Opinion and International Search Report issued Sep. 12, 2024 in Intl. Appl. No. PCT/IB2024/055759.

*Primary Examiner* — Javier G Blanco
(74) *Attorney, Agent, or Firm* — MEDLER FERRO WOODHOUSE & MILLS PLLC

(57) ABSTRACT

Prosthetic valve devices for implantation within a body or lumen that are configured for hemodynamic monitoring. The prosthetic valve device includes one or more sensors in electrical communication with an inductor formed by a portion of the frame or coupled to the frame of the prosthetic valve device. The sensor is configured to measure a flow parameter within the prosthesis. The inductor is configured to relay a signal to an external detector, the signal being associated with the flow parameter measured by the sensor.

20 Claims, 17 Drawing Sheets

(56) References Cited

U.S. PATENT DOCUMENTS

| | | | |
|---|---|---|---|
| 6,486,588 | B2 | 11/2002 | Doron et al. |
| 6,585,763 | B1 | 7/2003 | Keilman et al. |
| 6,592,518 | B2 | 7/2003 | Denker et al. |
| 6,645,143 | B2 | 11/2003 | Vantassel et al. |
| 6,669,647 | B2 | 12/2003 | Letort et al. |
| 6,743,173 | B2 | 6/2004 | Penner et al. |
| 6,840,956 | B1 | 1/2005 | Wolinsky et al. |
| 6,890,303 | B2 | 5/2005 | Fitz |
| 6,926,670 | B2 | 8/2005 | Rich et al. |
| 6,964,641 | B2 | 11/2005 | Cho et al. |
| 7,006,858 | B2 | 2/2006 | Silver et al. |
| 7,044,920 | B2 | 5/2006 | Letort |
| 7,097,658 | B2 | 8/2006 | Oktay |
| 7,181,261 | B2 | 2/2007 | Silver et al. |
| 7,232,460 | B2 | 6/2007 | Van Erlach et al. |
| 7,261,733 | B1 | 8/2007 | Brown et al. |
| 7,294,115 | B1 | 11/2007 | Wilk |
| 7,344,561 | B2 | 3/2008 | DiCarlo |
| 7,399,313 | B2 | 7/2008 | Brown et al. |
| 7,452,334 | B2 | 11/2008 | Gianchandani et al. |
| 7,488,345 | B2 | 2/2009 | Brown et al. |
| 7,684,872 | B2 | 3/2010 | Carney et al. |
| 7,704,209 | B2 | 4/2010 | Bennett et al. |
| 7,710,103 | B2 | 5/2010 | Powers et al. |
| 7,769,420 | B2 | 8/2010 | Silver et al. |
| 7,922,667 | B2 | 4/2011 | Gianchandani et al. |
| 8,075,490 | B2 | 12/2011 | Lofgren et al. |
| 8,095,225 | B2 | 1/2012 | Nippoldt et al. |
| 8,103,361 | B2 | 1/2012 | Moser |
| 8,118,751 | B2 | 2/2012 | Dobak |
| 8,187,317 | B2 | 5/2012 | Leprince et al. |
| 8,211,028 | B2 | 7/2012 | Karamanoglu et al. |
| 8,356,399 | B2 | 1/2013 | Kaplan |
| 8,380,294 | B2 | 2/2013 | Messier et al. |
| 8,401,643 | B2 | 3/2013 | Griswold et al. |
| 8,412,352 | B2 | 4/2013 | Griswold et al. |
| 8,419,638 | B2 | 4/2013 | Arne et al. |
| 8,465,436 | B2 | 6/2013 | Griswold |
| 8,478,378 | B2 | 7/2013 | Lal et al. |
| 8,512,252 | B2 | 8/2013 | Ludomirsky et al. |
| 8,515,559 | B2 | 8/2013 | Roberts et al. |
| 8,549,923 | B2 | 10/2013 | Chommeloux et al. |
| 8,554,315 | B2 | 10/2013 | Cho et al. |
| 8,628,461 | B2 | 1/2014 | Mohl |
| 8,696,735 | B2 | 4/2014 | Caro et al. |
| 8,727,996 | B2 | 5/2014 | Allan et al. |
| 8,784,475 | B2 | 7/2014 | Martinson et al. |
| 8,827,913 | B2 | 9/2014 | Havel et al. |
| 8,849,424 | B2 | 9/2014 | Nippoldt et al. |
| 8,864,676 | B2 | 10/2014 | Beasley et al. |
| 8,915,957 | B2 | 12/2014 | Arney et al. |
| 8,939,905 | B2 | 1/2015 | Schugt et al. |
| 9,220,906 | B2 | 12/2015 | Griswold et al. |
| 9,248,300 | B2 | 2/2016 | Rys et al. |
| 9,333,365 | B2 | 5/2016 | Zhao |
| 9,339,197 | B2 | 5/2016 | Griswold et al. |
| 9,351,648 | B2 | 5/2016 | Patras et al. |
| 9,468,517 | B2 | 10/2016 | Shalev |
| 9,533,096 | B2 | 1/2017 | Lebel et al. |
| 9,592,001 | B2 | 3/2017 | Barcelo et al. |
| 9,610,450 | B2 | 4/2017 | Zhao |
| 9,662,021 | B2 | 5/2017 | Chow et al. |
| 9,675,285 | B2 | 6/2017 | Christian |
| 9,717,421 | B2 | 8/2017 | Griswold et al. |
| 9,737,264 | B2 | 8/2017 | Braido et al. |
| 9,750,416 | B2 | 9/2017 | Liao et al. |
| 9,814,611 | B2 | 11/2017 | Cartledge et al. |
| 9,854,982 | B2 | 1/2018 | Allan et al. |
| 9,883,836 | B2 | 2/2018 | Deligianni et al. |
| 9,924,905 | B2 | 3/2018 | Kuraguntla et al. |
| 9,931,041 | B2 | 4/2018 | Spohn et al. |
| 9,987,129 | B2 | 6/2018 | Marcelli |
| 9,999,528 | B2 | 6/2018 | Kim et al. |
| 10,022,054 | B2 | 7/2018 | Najafi et al. |
| 10,052,069 | B2 | 8/2018 | Kavteladze |
| 10,117,621 | B2 | 11/2018 | Berger et al. |
| 10,130,288 | B2 | 11/2018 | Klueh et al. |
| 10,173,069 | B2 | 1/2019 | Guo et al. |
| 10,226,552 | B2 | 3/2019 | Slepian |
| 10,226,630 | B2 | 3/2019 | Greenhut et al. |
| 10,240,994 | B1 | 3/2019 | Xu |
| 10,307,067 | B1 | 6/2019 | Xu |
| 10,307,601 | B2 | 6/2019 | Mothilal et al. |
| 10,327,923 | B2 | 6/2019 | Laduca |
| 10,335,043 | B2 | 7/2019 | Jain et al. |
| 10,413,284 | B2 | 9/2019 | Mcnamara et al. |
| 10,433,791 | B2 | 10/2019 | Braido et al. |
| 10,441,221 | B2 | 10/2019 | Spindler |
| 10,537,287 | B2 | 1/2020 | Braido et al. |
| 10,624,732 | B2 | 4/2020 | Shimon |
| 10,667,754 | B2 | 6/2020 | Starr et al. |
| 10,729,569 | B2 | 8/2020 | Laduca et al. |
| 10,751,943 | B2 | 8/2020 | Grbic et al. |
| 10,869,748 | B2 | 12/2020 | Rosenberg et al. |
| 11,006,845 | B2 | 5/2021 | Kuraguntla et al. |
| 11,154,207 | B2 | 10/2021 | Campbell et al. |
| 11,172,885 | B2 | 11/2021 | Bozsak et al. |
| 11,284,840 | B1 | 3/2022 | Xu |
| 11,330,987 | B2 | 5/2022 | Jain et al. |
| 11,331,476 | B2 | 5/2022 | Capek et al. |
| 11,389,079 | B2 | 7/2022 | Hunter |
| 11,399,725 | B2 | 8/2022 | Greenhut |
| 11,432,731 | B2 | 9/2022 | Chun et al. |
| 11,445,924 | B2 | 9/2022 | Joseph |
| 11,445,978 | B2 | 9/2022 | Hunter |
| 11,471,275 | B2 | 10/2022 | Marquez et al. |
| 11,510,795 | B2 | 11/2022 | Arnault De La Menardiere et al. |
| 2002/0183628 | A1 | 12/2002 | Reich et al. |
| 2003/0100938 | A1 | 5/2003 | Rubenchik et al. |
| 2003/0125790 | A1 | 7/2003 | Fastovsky et al. |
| 2004/0210118 | A1 | 10/2004 | Letort |
| 2005/0124896 | A1 | 6/2005 | Richter et al. |
| 2005/0165317 | A1 | 7/2005 | Turner et al. |
| 2005/0277839 | A1 | 12/2005 | Alderman et al. |
| 2006/0149347 | A1 | 7/2006 | Hayashi et al. |
| 2006/0155366 | A1 | 7/2006 | LaDuca et al. |
| 2006/0161225 | A1 | 7/2006 | Sormann et al. |
| 2007/0038292 | A1 | 2/2007 | Danielpour |
| 2007/0150051 | A1 | 6/2007 | Arnault De La Menardiere et al. |
| 2007/0219623 | A1 | 9/2007 | Palmaz |
| 2007/0244373 | A1 | 10/2007 | Osypka |
| 2008/0033527 | A1 | 2/2008 | Nunez et al. |
| 2008/0058652 | A1 | 3/2008 | Payne |
| 2008/0139951 | A1 | 6/2008 | Patangay et al. |
| 2008/0281210 | A1 | 11/2008 | Nunez et al. |
| 2009/0005859 | A1 | 1/2009 | Keilman |
| 2009/0036975 | A1 | 2/2009 | Ward et al. |
| 2009/0048524 | A1 | 2/2009 | Wildau et al. |
| 2009/0062669 | A1 | 3/2009 | Akingba |
| 2009/0210050 | A1 | 8/2009 | Van Tassel et al. |
| 2009/0259112 | A1 | 10/2009 | Hyde et al. |
| 2009/0299198 | A1 | 12/2009 | Carney et al. |
| 2010/0217136 | A1 | 8/2010 | Turner et al. |
| 2010/0228135 | A1 | 9/2010 | Schulhauser et al. |
| 2010/0298720 | A1 | 11/2010 | Potkay |
| 2012/0296222 | A1 | 11/2012 | Griswold et al. |
| 2013/0053711 | A1 | 2/2013 | Kotlanka et al. |
| 2013/0109933 | A1 | 5/2013 | Wittchow et al. |
| 2014/0018643 | A1 | 1/2014 | Achkar et al. |
| 2014/0081154 | A1 | 3/2014 | Toth |
| 2014/0107771 | A1 | 4/2014 | Berreklouw |
| 2014/0296962 | A1 | 10/2014 | Cartledge et al. |
| 2014/0336743 | A1 | 11/2014 | Zotz |
| 2015/0119633 | A1 | 4/2015 | Haselby et al. |
| 2015/0126833 | A1 | 5/2015 | Anderson et al. |
| 2015/0320357 | A1 | 11/2015 | Kuraguntla et al. |
| 2015/0320424 | A1 | 11/2015 | Gourlay |
| 2015/0327777 | A1 | 11/2015 | Kostic et al. |
| 2015/0342761 | A1 | 12/2015 | Marton et al. |
| 2016/0045316 | A1* | 2/2016 | Braido .................. A61F 2/2445 623/2.38 |
| 2016/0256107 | A1 | 9/2016 | Gupta et al. |
| 2016/0310077 | A1 | 10/2016 | Hunter et al. |
| 2017/0020442 | A1 | 1/2017 | Flitsch et al. |

(56) References Cited

U.S. PATENT DOCUMENTS

| | | | |
|---|---|---|---|
| 2017/0105635 | A1 | 4/2017 | Cho et al. |
| 2017/0165060 | A1 | 6/2017 | Barongan |
| 2017/0196509 | A1* | 7/2017 | Hunter .................. A61F 2/2472 |
| 2017/0202691 | A1 | 7/2017 | Labelle et al. |
| 2017/0258585 | A1* | 9/2017 | Marquez ............... A61F 2/2409 |
| 2017/0304516 | A1 | 10/2017 | Burnes et al. |
| 2018/0035898 | A1 | 2/2018 | Gunderson |
| 2018/0049877 | A1 | 2/2018 | Venkatasubramanian |
| 2018/0103899 | A1 | 4/2018 | Cahan et al. |
| 2018/0228371 | A1 | 8/2018 | McClain |
| 2018/0289520 | A1 | 10/2018 | Arnault De La Menardiere et al. |
| 2018/0317925 | A1 | 11/2018 | Pillai |
| 2018/0344461 | A1 | 12/2018 | Wilson et al. |
| 2019/0159684 | A1 | 5/2019 | Bozsak et al. |
| 2019/0167452 | A1 | 6/2019 | Palmaz et al. |
| 2019/0175111 | A1 | 6/2019 | Genereux et al. |
| 2019/0175372 | A1 | 6/2019 | Boyden et al. |
| 2019/0175883 | A1 | 6/2019 | Wessler et al. |
| 2019/0183354 | A1 | 6/2019 | Rowe |
| 2019/0246916 | A1* | 8/2019 | Kuraguntla .......... A61B 5/0031 |
| 2020/0155063 | A1 | 5/2020 | Kuraguntla et al. |
| 2020/0196953 | A1 | 6/2020 | Degen et al. |
| 2020/0222185 | A1 | 7/2020 | Kappetein et al. |
| 2020/0222214 | A1 | 7/2020 | Arnault De La Menardiere et al. |
| 2020/0237534 | A1 | 7/2020 | Manolidis |
| 2020/0261224 | A1 | 8/2020 | Gross |
| 2020/0268256 | A1 | 8/2020 | Harding et al. |
| 2020/0268316 | A1 | 8/2020 | Hunter |
| 2020/0289057 | A1 | 9/2020 | An et al. |
| 2020/0319268 | A1 | 10/2020 | Green et al. |
| 2020/0323616 | A1 | 10/2020 | Lashinski et al. |
| 2020/0345289 | A1 | 11/2020 | Hettrick et al. |
| 2020/0352758 | A1 | 11/2020 | MacTaggart et al. |
| 2020/0383583 | A1 | 12/2020 | Hendriks et al. |
| 2021/0007610 | A1 | 1/2021 | Hendriks et al. |
| 2021/0022610 | A1 | 1/2021 | Domnich et al. |
| 2021/0022897 | A1 | 1/2021 | Arnault De La Menardiere et al. |
| 2021/0038094 | A1* | 2/2021 | Sweeney ................... A61F 2/86 |
| 2021/0052385 | A1 | 2/2021 | Yaron et al. |
| 2021/0121179 | A1 | 4/2021 | Ben-David et al. |
| 2021/0204828 | A1 | 7/2021 | Schmidt et al. |
| 2021/0236112 | A1 | 8/2021 | Vidlund et al. |
| 2021/0267759 | A1 | 9/2021 | Yaron |
| 2021/0298930 | A1 | 9/2021 | Sherburne |
| 2021/0315700 | A1 | 10/2021 | Forsell |
| 2021/0338463 | A1 | 11/2021 | Mukerjee et al. |
| 2021/0379359 | A1 | 12/2021 | Schellenberg et al. |
| 2021/0401302 | A1 | 12/2021 | Phillips |
| 2022/0015901 | A1 | 1/2022 | Dibie |
| 2022/0039671 | A1 | 2/2022 | Fahey |
| 2022/0039752 | A1 | 2/2022 | Hunter |
| 2022/0047162 | A1 | 2/2022 | Hunter et al. |
| 2022/0054267 | A1 | 2/2022 | Bar et al. |
| 2022/0133237 | A1 | 5/2022 | Reiner |
| 2022/0151493 | A1 | 5/2022 | Rothfuss et al. |
| 2022/0167922 | A1 | 6/2022 | Gross et al. |
| 2022/0192502 | A1 | 6/2022 | Eslami et al. |
| 2022/0192677 | A1 | 6/2022 | Wedul et al. |
| 2022/0244123 | A1 | 8/2022 | Fenner et al. |
| 2022/0257128 | A1 | 8/2022 | Goldberg et al. |
| 2022/0257379 | A1 | 8/2022 | Dvorsky et al. |
| 2022/0265157 | A1 | 8/2022 | Charthad et al. |
| 2022/0287580 | A1 | 9/2022 | Yeo et al. |
| 2022/0287851 | A1* | 9/2022 | Goldberg .............. A61F 2/2418 |
| 2022/0296167 | A1 | 9/2022 | Carpenter |

* cited by examiner

HEART VALVE PROSTHESES WITH SENSOR FOR HEMODYNAMIC MONITORING

CROSS-REFERENCE TO RELATED APPLICATIONS

This application claims the benefit of U.S. Provisional Patent Application Ser. No. 63/508,069, filed Jun. 14, 2023, the entire content of which is incorporated herein by reference.

FIELD OF THE INVENTION

The present disclosure relates generally to prosthetic valves, and more particularly to a prosthetic valve device including one or more integrated sensor for hemodynamic monitoring.

BACKGROUND

Natural heart valves, such as aortic valves, mitral valves, pulmonary valves and tricuspid valves, often become damaged by disease in such a manner that they fail to maintain blood flow in a single direction. A malfunctioning heart valve may be stenotic (i.e., heart valve leaflets fail to fully open) or regurgitant (i.e., heart valve leaflets fail to fully close and/or seal). Maintenance of blood flow in a single direction through the heart valve is important for proper flow, pressure and perfusion of blood through the body. Hence, a heart valve that does not function properly may noticeably impair the function of the heart.

Cardiac valve prostheses are well known in the treatment of heart disease to replace malfunctioning heart valves. Heart valve replacement generally has been accomplished by major open-heart surgery. This is a serious operation that requires general anesthesia, full cardiopulmonary bypass with complete cessation of cardiopulmonary activity, an extended hospitalization stay, and several more weeks to months of recuperation time. For some patients, open heart surgery is not an option because of the critical condition of the patient, advanced age, existing comorbidities, or other physical limitations.

In addition to replacing malfunctioning heart valves, there is a congenital heart defect patient population that may have fewer than four valves or valves that were removed or rendered incompetent by surgical procedures. These patients tend to be younger with full lives and future valve procedures ahead of them. The patients may present without a typical existing valve annulus and instead have a less discrete, often dilated area where a healthy valve would have typically formed. These dilated areas may also spiral or curve as the patient's heart, other organs, and skeletal anatomy developed around a heart without one or more valves and accommodated based on revised positions, pressures, and flows. In addition to the more traditional adult population, the congenital population may need for a heart valve to deploy in unusually challenging anatomical condition, also requiring hemodynamic performance while conforming to these varied anatomies without regurgitating, buckling, or kinking.

The continued evaluation of heart valve failure is crucial for the lifetime management of a patient. Traditionally, patients that had previously received replacement valves are required to make consistent doctor visits to check on the status of their heart, the functionality of the replacement valve, and the flow of blood through the replacement valve. These consistent visits can be both mentally and physically taxing on a patient.

Thus, there is a continuing need to improve upon the monitoring capabilities of devices available for heart valve replacement.

SUMMARY

According to a first embodiment hereof, the present disclosure provides a prosthesis for implantation within a body or lumen. The prosthesis includes a frame including a plurality of rows of struts and crowns formed between adjacent pairs of said struts, each row having a first set of crowns and a second set of crowns with the first set of crowns being disposed closer to an inflow end of the prosthesis than the second set of crowns. The frame has a first longitudinal portion and a second longitudinal portion disposed axially adjacent to the first longitudinal portion. The second longitudinal portion forms at least two rows of the plurality of rows and the first longitudinal portion forms at least two rows of the plurality of rows. The second longitudinal portion is formed from a single composite wire having a first end and a second end opposing the first end. The composite wire has a core of a first material, an intermediate layer of a second material, and an outer layer of a third material, the third material being an electrically insulative material. A prosthetic valve component is disposed within the frame. At least one sensor is configured to measure a flow parameter within the prosthesis. A first end of the sensor is attached to the first end of the single component wire and a second end of the sensor is attached to the second end of the single composite wire. The second longitudinal portion forms an inductor configured to relay a signal to an external detector, the signal being associated with the at least one sensor.

In an aspect of the first embodiment, the first longitudinal portion may form three rows of the plurality of rows and the second longitudinal portion may form three rows of the plurality of rows. A length of the first longitudinal portion may be substantially equal to a length of the second longitudinal portion. The second set of crowns of each row may be disposed against and attached to the first set of crowns of an adjacent row by at least two axial suture loops extending over adjacent crowns. The first longitudinal portion may include an inflow end of the prosthesis and the second longitudinal portion may include an outflow end of the prosthesis. The first longitudinal portion may be stronger than the second longitudinal portion. The first longitudinal portion may include an inflow stent disposed at the inflow end of the prosthesis and at least one body stent disposed between the second longitudinal portion and the inflow stent, where each of the inflow stent and the at least one body stent is a sinusoidal patterned radially expandable ring that forms one row of the plurality of rows. Each sinusoidal patterned radially expandable ring may be composed of nitinol wire.

In an aspect of the first embodiment, the prosthetic valve component may be disposed adjacent to a junction between the first longitudinal portion and the second longitudinal portion. The first longitudinal portion of the frame may be formed from one or more solid wires of the second material. The first material may be platinum and the second material may be nitinol. The at least one sensor may be a passive capacitive pressure sensor. The flow parameter to be measured may be blood pressure. The at least one sensor may include a first sensor and the prosthesis may further include a second sensor, and the flow parameter to be measured may be a gradient between the first sensor and the second sensor. The second sensor may be disposed closer to an inflow end of the prosthesis and the first sensor is disposed closer to an outflow end of the prosthesis.

In an aspect of the first embodiment, the at least one sensor may be a compliant sensor or a rigid sensor. The at least one sensor may include a plurality of sensors and each sensor of the plurality of sensors is electrically coupled to the second longitudinal portion of the frame. The at least one sensor may be wireless and/or batteryless. The external detector may be configured to power the at least one sensor and communicate with the inductor, and the signal relayed by the inductor to the external detector may be achieved through inductive coupling. The inductor may be a first inductor and the at least one sensor may be a first sensor, where the first longitudinal portion is formed from a second single composite wire having a first end and a second end opposing the first end. The composite wire has a core of the first material, an intermediate layer of the second material, and an outer layer of the third material. The prosthesis further includes a second sensor electrically coupled to the first longitudinal portion of the frame. The second sensor is configured to measure the flow parameter within the prosthesis. A first end of the second sensor is attached to the first end of the second single component wire and a second end of the second sensor is attached to the second end of the second single composite wire. The first longitudinal portion forms a second inductor configured to relay a signal to the external detector, the signal being associated with the second sensor.

In an aspect of the first embodiment, the inductor may be a first inductor and the at least one sensor is a first sensor, and the prosthesis further includes a second sensor electrically coupled to the first longitudinal portion of the frame. The second sensor is configured to measure the flow parameter within the prosthesis. The prosthesis further includes a coil having a plurality of windings coupled to the first longitudinal portion of the frame and electrically coupled to the second sensor. The coil forms a second inductor configured to relay a signal to the external detector, the signal being associated with the second sensor. The coil may be formed from stainless steel coated with a polymer and may have a sinusoidal configuration along its length.

According to a second embodiment hereof, the present disclosure provides a prosthesis for implantation within a body or lumen. The prosthesis includes a tubular graft defining a lumen that extends from an inflow end to an outflow end, a prosthetic valve component disposed within the lumen of the tubular graft, and a frame attached to the tubular graft. The frame includes an inflow stent attached to the inflow end of the tubular graft, an outflow stent attached to the outflow end of the tubular graft, and a plurality of body stents attached to the tubular graft and disposed between the inflow stent and the outflow stent. Each stent of the plurality of body stents, the inflow stent, and the outflow stent is a sinusoidal patterned radially expandable ring having a first set of crowns and a second set of crowns. A coil having a plurality of windings is woven into the tubular graft to encircle a portion of the frame. At least one sensor is electrically coupled to the coil and is configured to measure a flow parameter within the prosthesis. The coil forms an inductor configured to relay a signal to an external detector, the signal being associated with the at least one sensor.

In an aspect of the second embodiment, a first body stent of the plurality of body stents may be disposed directly adjacent to the inflow stent and a second body stent of the plurality of body stents may be disposed directly adjacent to the outflow stent. Each of the inflow stent, the outflow stent, and each stent of the plurality of body stents is a sinusoidal patterned radially expandable ring having a first set of crowns and a second set of crowns. Each of the inflow stent, the outflow stent, and the plurality of body stents may be composed of nitinol wire. The coil may be formed from stainless steel coated with a polymer. The coil may have a sinusoidal configuration along its length. The second set of crowns of each stent may be disposed against and attached to the first set of crowns of an adjacent stent by at least two axial suture loops extending over adjacent crowns. The at least one sensor may be a passive capacitive pressure sensor.

In an aspect of the second embodiment, the flow parameter to be measured may be blood pressure. The at least one sensor may include a first sensor and the prosthesis further includes a second sensor, and the flow parameter is a gradient between the first sensor and the second sensor. The second sensor may be disposed closer to an inflow end of the prosthesis and the first sensor may be disposed closer to an outflow end of the prosthesis. The at least one sensor may be a compliant sensor or a rigid sensor. The at least one sensor may include a plurality of sensors and each sensor of the plurality of sensors is electrically coupled to the coil. The at least one sensor may be wireless and/or batteryless. The external detector may be configured to power the at least one sensor and communicate with the inductor. The signal relayed by the inductor to the external detector may be achieved through inductive coupling.

According to a third embodiment hereof, the present disclosure provides a method for measuring a flow parameter within a prosthesis implanted within a lumen of a body. The method includes measuring the flow parameter with at least one sensor, communicating the flow parameter to the inductor in electrical communication with the at least one sensor, relaying, via the inductor, a signal associated with the at least one sensor, receiving the signal via an antenna of the external detector, and displaying the flow parameter measured by the at least one sensor on a display integral or connected to the external detector.

In an aspect of the third embodiment, the flow parameter being measured may be blood pressure. Alternatively, the flow parameter to be measured may be a blood flow rate. The method may further include the step of holding the external detector against an external surface of a patient having the prosthetic valve device implanted therein. Upon holding the external detector in place against the external surface, the external detector may power the at least one sensor. The step of relaying the signal may be achieved through inductive coupling between the inductor of the prosthetic valve and the antenna of the external device.

BRIEF DESCRIPTION OF THE DRAWINGS

The accompanying figures, which are incorporated herein, form part of the specification and illustrate embodiments of a delivery system. Together with the description, the figures further explain the principles of and enable a person skilled in the relevant arts to make, use, and implant the prosthesis described herein. In the drawings, like reference numbers indicate identical or functionally similar elements.

DETAILED DESCRIPTION OF THE INVENTION

Figure 1:
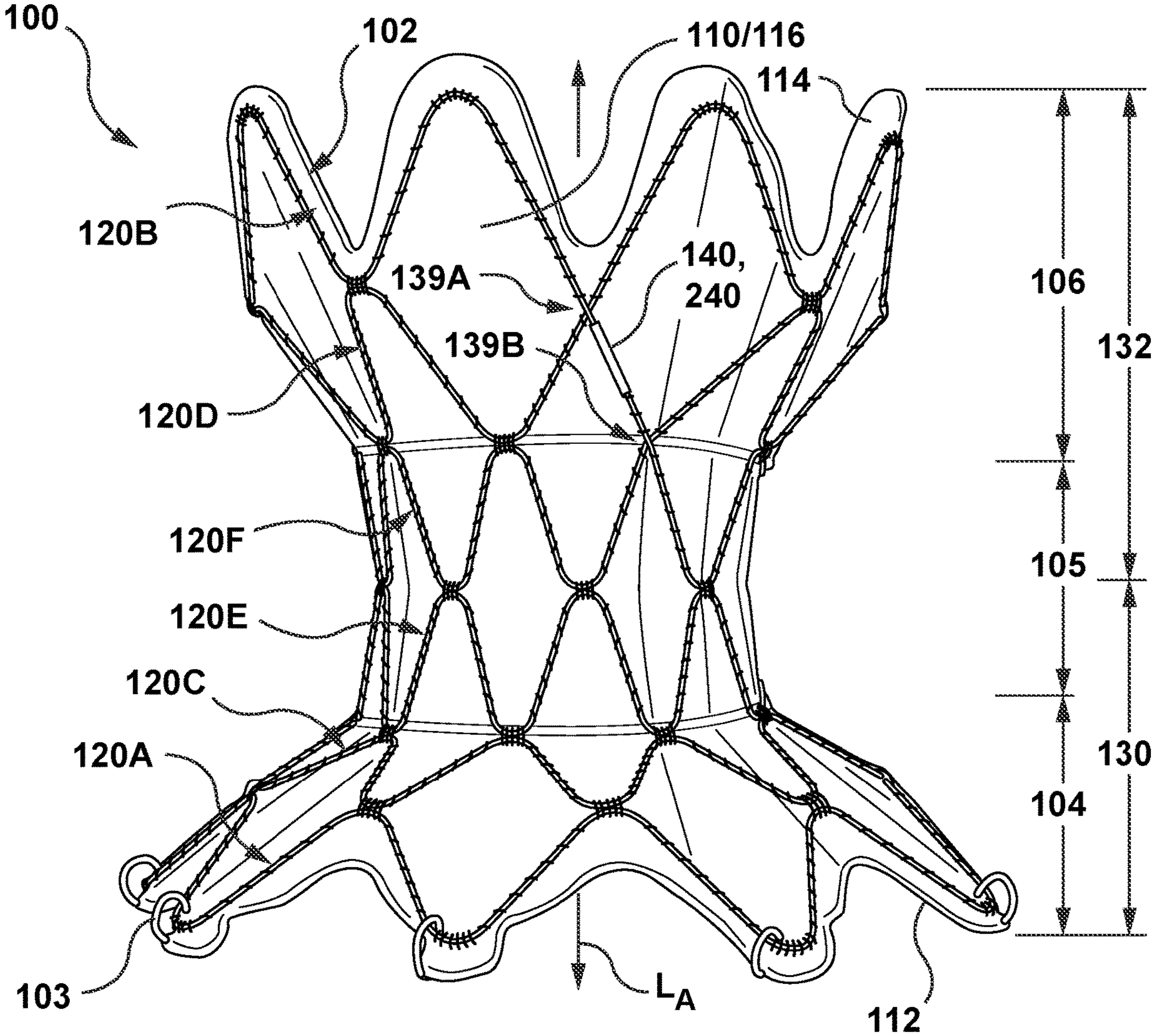
FIG. 1 is a side view of a prosthetic valve device according to an aspect of the present disclosure, wherein the prosthetic valve device is shown in its radially expanded or deployed configuration, and wherein the prosthetic valve device includes a sensor in electrical communication with an inductor formed by a stent of the prosthetic valve device.

Specific embodiments of the present invention are now described with reference to the figures, wherein like reference numbers indicate identical or functionally similar elements. Unless otherwise indicated, the terms "distal" and "proximal", when used in the following description to refer to a shaft, a sheath, or a delivery device, are with respect to a position or direction relative to the treating clinician. Thus, "distal" and "distally" refer to positions distant from, or in a direction away from the treating clinician, and the terms "proximal" and "proximally" refer to positions near, or in a direction toward the treating clinician. The terms "distal" and "proximal", when used in the following description to refer to a device to be implanted into a vessel, such as a heart prosthetic valve device, are used with reference to the direction of blood flow. Thus, "distal" and "distally" refer to positions in a downstream direction with respect to the direction of blood flow, and the terms "proximal" and "proximally" refer to positions in an upstream direction with respect to the direction of blood flow.

In addition, the term "self-expanding" is used in the following description with reference to one or more stent structures of the prostheses hereof and is intended to convey that the structures are shaped or formed from a material that can be provided with a mechanical memory to return the structure from a radially compressed or constricted radially compressed configuration to a radially expanded deployed configuration. Non-exhaustive illustrative self-expanding materials include stainless steel, a pseudo-elastic metal such as a nickel titanium alloy or nitinol, various polymers, or a so-called super alloy, which may have a base metal of nickel, cobalt, chromium, or other metal. Mechanical memory may be imparted to a wire or stent structure by thermal treatment to achieve a spring temper in stainless steel, for example, or to set a shape memory in a susceptible metal alloy, such as nitinol. Various polymers that can be made to have shape memory characteristics may also be suitable for use in embodiments hereof to include polymers such as polynorborene, trans-polyisoprene, styrene-butadiene, and polyurethane. As well poly L-D lactic copolymer, oligo caprylactone copolymer and poly cyclo-octine can be used separately or in conjunction with other shape memory polymers.

Embodiments hereof relate to prosthetic valve devices for implantation within a body or lumen that is configured for hemodynamic monitoring. The prosthetic valve device includes one or more sensors in electrical communication with an inductor formed by a portion of the frame or coupled to the frame of the prosthetic valve device. The sensor is configured to measure a flow parameter within the prosthesis. The inductor is configured to relay a signal to an external detector, the signal being associated with the flow parameter measured by the sensor. As such, the inductor functions or operates as an antenna to relay the signal associated with the flow parameter to the external detector.

With reference to the embodiment of FIGS. 1-6E, a prosthetic valve device 100 includes an expandable frame 102, a tubular graft 110, and a prosthetic valve component 108 disposed within and secured to the frame 102 and/or the tubular graft 110. The frame may be considered to include a first longitudinal portion 130 and a second longitudinal portion 132. The prosthetic valve device 100 includes one or more sensors in electrical communication with an inductor 138 formed by the second longitudinal portion 132 of the frame 102 of the prosthetic valve device 100. A sensor 140 according to a first embodiment suitable for use with the prosthetic valve device 100 is shown and described in more detail with respect to FIGS. 6A-6C, and a sensor 240 according to a second embodiment suitable for use with the prosthetic valve device 100 is shown and described in more detail with respect to FIG. 6D. Stated another way, each of the sensor 140 and the sensor 240 is suitable for use in embodiments hereof. The frame 102 is presented by way of example only, and sensor 140, 240 and the inductor 138 may be incorporated into frames of other shapes and designs. There is no intention of being bound by any expressed or implied theory presented in the preceding technical field, background, brief summary or the following detailed description.

Figure 2:
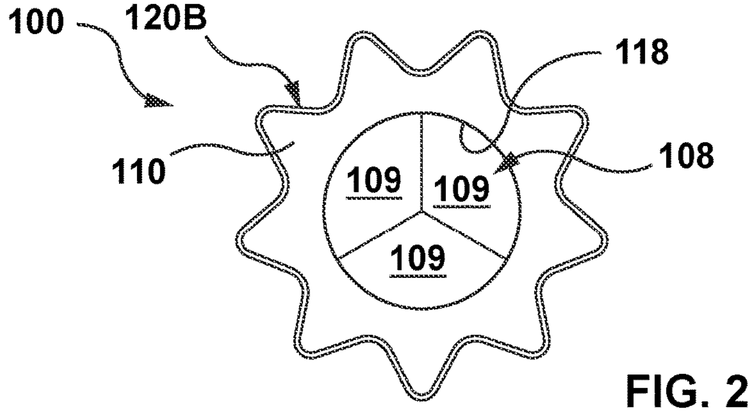
FIG. 2 is an end view of the prosthetic valve device of FIG. 1.

A side view and an end view of the prosthetic valve device 100 are shown in FIG. 1 and FIG. 2, respectively. In this embodiment, the frame 102 is self-expanding or self-expandable and is configured to be radially compressed into a reduced-diameter crimped configuration (not shown) for delivery within a vasculature and to return to a radially expanded or deployed configuration, which is shown in FIG. 1 and FIG. 2. Stated another way, the prosthetic valve device 100 has a radially compressed configuration for delivery within a vasculature and a radially expanded configuration for deployment at a treatment site. The prosthetic valve device 100 includes a plurality of attachment members 103 on or near the inflow end 104 for coupling the prosthetic valve device 100 to a delivery system (not shown). For delivery, the prosthetic valve device 100 is radially compressed into the reduced-diameter crimped configuration onto the delivery system for delivery within a vasculature. As known in the art, the delivery system includes an inner shaft that receives the prosthetic valve device 100 on a distal portion thereof and an outer sheath or capsule that is configured to compressively retain the prosthetic valve device 100 on the distal portion of the inner shaft during delivery. Stated another way, the outer sheath or capsule surrounds and constrains the prosthetic valve device 100 in the radially compressed or crimped configuration. An exemplary delivery system for delivering the prosthetic valve device 100 is described in U.S. Pat. No. 9,364,324 to Rafice et al., which is hereby incorporated by reference in its entirety. However, it will be apparent to one of ordinary skill in the art that other delivery systems may be utilized and that the components of the delivery system may vary depending upon the configuration and structure of the prosthetic valve device that is being delivered.

Figure 3:
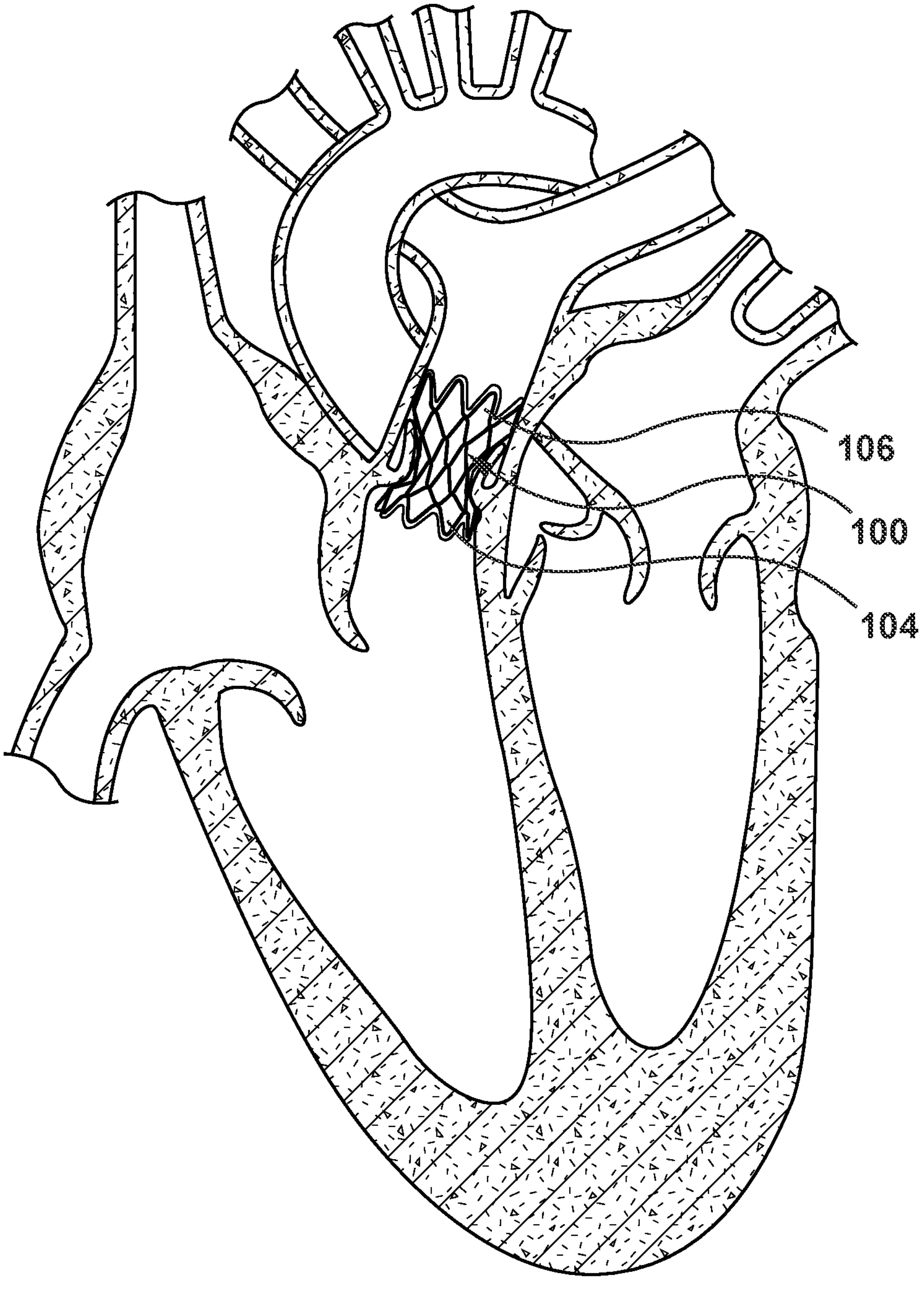
FIG. 3 depicts the prosthetic valve device of FIG. 1 implanted in situ at a treatment site according to an aspect of the present disclosure, wherein the treatment site is a native right ventricular outflow tract (RVOT).
Figure 4A:
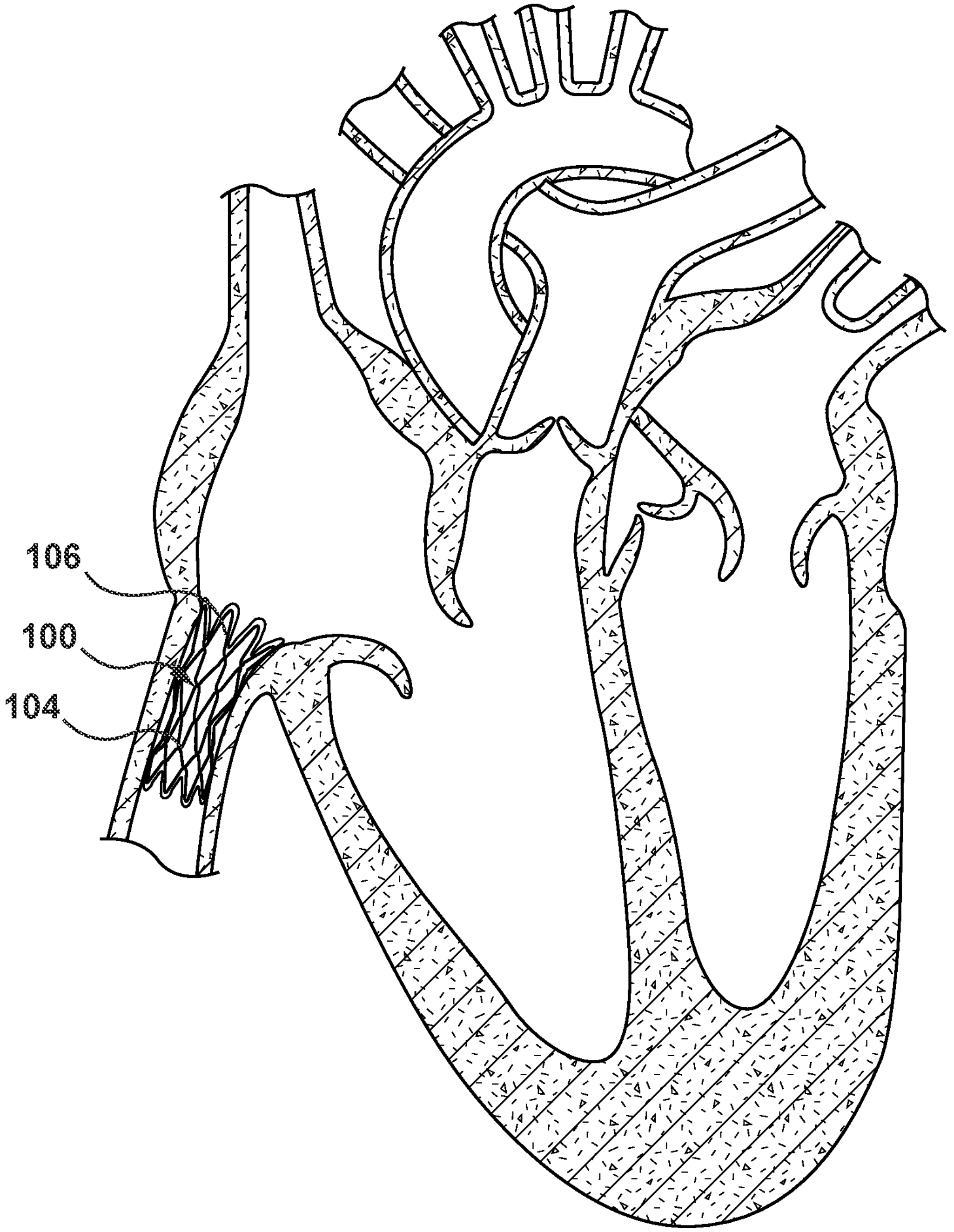
FIG. 4A depicts the prosthetic valve device of FIG. 1 implanted in situ at a treatment site according to another aspect of the present disclosure, wherein the treatment site is an Inferior Vena Cava (IVC).
Figure 4B:
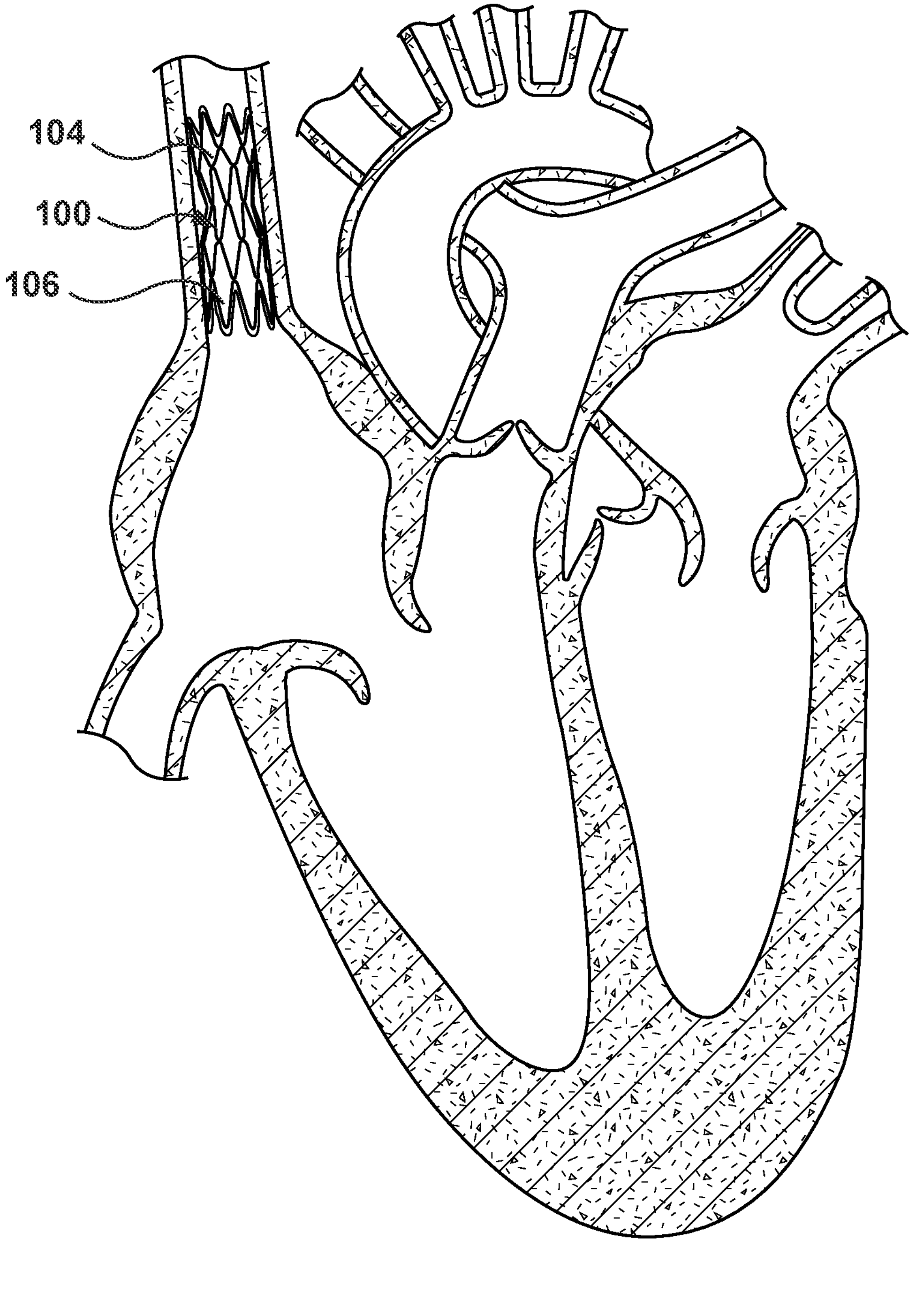
FIG. 4B depicts the prosthetic valve device of FIG. 1 implanted in situ at a treatment site according to another aspect of the present disclosure, wherein the treatment site is a Superior Vena Cava (SVC).

In an embodiment, the prosthetic valve device 100 is an infundibular reducer device configured to be implanted in the pulmonary valve or the infundibulum. FIG. 3 depicts the prosthetic valve device 100 implanted in situ at a treatment site, and the treatment site is a native right ventricular outflow tract (RVOT). In FIG. 3, the native right ventricular outflow tract (RVOT) which includes a native pulmonary valve. However, as will be understood by one of ordinary skill in the art, a native right ventricular outflow tract (RVOT) may or may not include a native pulmonary valve. The prosthetic valve device 100 may be used in anatomic locations other than the infundibulum, such as other locations within the right ventricular outflow tract and other locations in or near the heart. The purpose of such devices is to allow replacement or prosthetic valves, such as pericardial heart valves, for example, having a smaller diameter than the diameter of the implanted site (e.g., the right ventricular outflow tract) to be implanted. However, other uses of the invention, such as implanting the prosthetic valves described herein at different locations in the body, are contemplated and are not limited to those discussed in the application. For example, the prosthetic valve device 100 may be configured for placement within a different heart valve, i.e., the aortic, mitral, or tricuspid valve, or may be utilized with a prosthetic valve device configured for placement within a venous valve or within other body passageways where it is deemed useful. For example, in another embodiment hereof, the prosthetic valve device 100 is configured to be implanted in the inferior vena cava (IVC) or the superior vena cava (SVC). For example, FIG. 4A depicts the prosthetic valve device 100 implanted in situ at a treatment site and the treatment site is an inferior vena cava (IVC). FIG. 4B depicts the prosthetic valve device 100 implanted in situ at a treatment site and the treatment site is a superior vena cava (SVC). In another embodiment (not shown), a first prosthetic valve device 100 may be implanted in an inferior vena cava (IVC) and a second prosthetic valve device 100 may be implanted in a superior vena cava (SVC). For example, placement of multiple prosthetic valve devices 100 may be utilized in patients with hyperplastic left heart syndrome there may be both lower and upper. Furthermore, multiple prosthetic valve devices 100 may be implanted at spaced apart locations to balance the flow in any vascular structures (such as but not limited to the right pulmonary artery compared to the left pulmonary artery), and the sensor 140, 240 may be utilized to monitor the flow balance and the disease progression.

The tubular graft 110 of the prosthetic valve device 100 has a first or inflow end 112, a second or outflow end 114, and a body 116 therebetween which defines a central lumen 118 that extends from the inflow end 112 to the outflow end 114. The central lumen 118 may also be considered a central lumen through the prosthetic valve device 100. A longitudinal axis LA of the prosthetic valve device 100 is defined by or extends parallel to the central lumen 118 of the tubular graft 110. In an embodiment, the inflow end 112 of tubular graft 110 may be referred to as a proximal end of tubular graft 110 and a proximal end of prosthetic valve device 100, which may be the end that is coupled to the delivery system, and the outflow end 114 of tubular graft 110 may be referred to as a distal end of graft 114 and a distal end of prosthetic valve device 100. The tubular graft 110 encloses or lines the frame 102 as would be known to one of ordinary skill in the art of prosthetic tissue valve construction. The tubular graft 110 may be a natural or biological material such as pericardium or another membranous tissue such as intestinal submucosa. Alternatively, the tubular graft 110 may be a knit or low-porosity woven fabric, such as polyester, Dacron fabric, or PTFE, which creates a one-way fluid passage when attached to the stent. In one embodiment, the tubular graft 110 may be a knit or woven polyester, such as a polyester or PTFE knit, which can be utilized when it is desired to provide a medium for tissue ingrowth and the ability for the fabric to stretch to conform to a curved surface or may instead be ultra-high molecular weight polyethylene (UHMWPE), cotton, or the like. Polyester velour fabrics may alternatively be used, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example.

The prosthetic valve component 108 is positioned or disposed within the center lumen 118 of the tubular graft 110. The prosthetic valve component 108 is attached to (i.e., affixed to, held by, retained by, etc.) the frame 102 along its ends and is sutured or otherwise attached within the frame 102 and/or the tubular graft 110. The prosthetic valve component 108 is capable of blocking flow in one direction to regulate flow there through via valve leaflets 109 that may form a bicuspid or tricuspid replacement valve. In the embodiment of FIGS. 1 and 2, the prosthetic valve component 108 includes three leaflets 109 or a tricuspid leaflet configuration, although a bicuspid leaflet configuration may alternatively be used in embodiments hereof. The leaflets 109 may be formed of a variety of materials including biological materials and polymers. Biological material includes homograft, allograft, or xenograft, with xenograft being common and well accepted and usually from bovine, ovine, swine or porcine pericardium, or a combination thereof. Polymers include expanded TEFLON™ polymers, high density polyethylene, polyurethane, and combinations thereof. Some examples of prosthetic valve components that may be used in the invention are described in U.S. Pat. Nos. 6,719,789 and 5,480,424, issued to Cox, which are incorporated herein by reference. With certain prosthetic leaflet materials, it may be desirable to coat one or both sides of the replacement valve leaflet with a material that will prevent or minimize overgrowth. It is further desirable that the prosthetic leaflet material is durable and not subject to stretching, deforming, or fatigue.

In this embodiment, the frame 102 has an expanded, longitudinally asymmetric hourglass configuration including three longitudinal sections of a relatively enlarged inflow end 104, a relatively enlarged outflow end 106, and a midsection 105 extending between the first and second ends 104, 106. The inflow end 104 may also be referred to herein as the proximal or first end, and the outflow end 106 may also be referred to herein as the distal or second end. The midsection 105 is generally cylindrical in shape with a smaller diameter than the inflow and outflow ends 104, 106. One advantage of the midsection 105 having a smaller diameter than the inflow and outflow ends 104, 106 is to allow at least a portion of the midsection 105 of the frame 102 to hold or retain the prosthetic valve component 108 in the central lumen 118 of the tubular graft 110, when the prosthetic valve component 108 has a smaller diameter than the lumen in which the prosthetic valve device 100 is to be placed. The larger diameters of the inflow and outflow ends 104, 106 allow the prosthetic valve device 100 to be secured in place in a tubular organ, or a valved anatomic site, having a diameter larger than that of the prosthetic valve component 108 but smaller than the expanded diameter of the inflow and outflow ends 104, 106. The inflow and outflow ends 104, 106 are flared, such that they gradually increase in diameter from where the inflow and outflow 104, 106 extend from the midsection 105.

The frame 102 includes a plurality of rows 120A, 120B, 120C, 120D, 120E, 120F, herein collectively referred to as rows 120. As will be described in more detail herein, the rows 120 are formed by at least two radially compressible stents or scaffolds that are coupled to the tubular graft 110 for supporting the tubular graft 110 and are operable to self-expand into apposition with an interior wall of a body vessel. The stents forming the rows 120 have sufficient radial spring force and flexibility to conformingly engage the prosthetic valve device 100 with the surrounding native anatomy, i.e., to provide a leak-resistant seal. In the embodiment depicted in FIG. 1, the prosthetic valve device 100 is shown in its radially expanded or deployed configuration and includes a series of six rows 120. Although shown with six rows 120, it will be understood by one of ordinary skill in the art that the prosthetic valve device 100 may include a greater or smaller number of rows depending upon the desired length of the prosthetic valve device 100 and/or the intended application thereof. The stents forming the rows 120 are coupled to the tubular graft 110 by stitches or other means known to those of skill in the art. In the embodiment shown in FIG. 1, the stents forming the rows 120 are coupled to an outside surface of the tubular graft 110. However, the stents forming the rows 120 may alternatively be coupled to an inside surface of the tubular graft 110.

For description purposes only, the row that is coupled adjacent and proximate to the inflow end 112 of the tubular graft 110 is referred to herein as an inflow row 120A and the row that is coupled adjacent and proximate to the outflow end 114 of the tubular graft 110 is referred to herein as outflow row 120B. The frame 102 also includes a plurality of body rows 120C, 120D, 120E, 120F that are attached to the tubular graft 110 and disposed between the inflow row 120A and the outflow row 120B. A first body row 120C of the plurality of body rows is disposed directly adjacent to the inflow row 120A and a second body row 120D of the plurality of body rows is disposed directly adjacent to the outflow row 120B. The inflow end 104 of the frame 102 includes the inflow row 120A and the first body row 120C, the midsection 105 of the frame 102 includes the third body row 120E and the fourth body row 120F, and the outflow end 106 of the frame 102 includes the outflow row 120B and the second body row 120D. The third and fourth body rows 120E, 120F are longitudinally disposed between the first and second body rows 120C, 120D, and are oriented to extend substantially parallel to the longitudinal axis LA of the prosthetic valve device 100.

Figure 5:
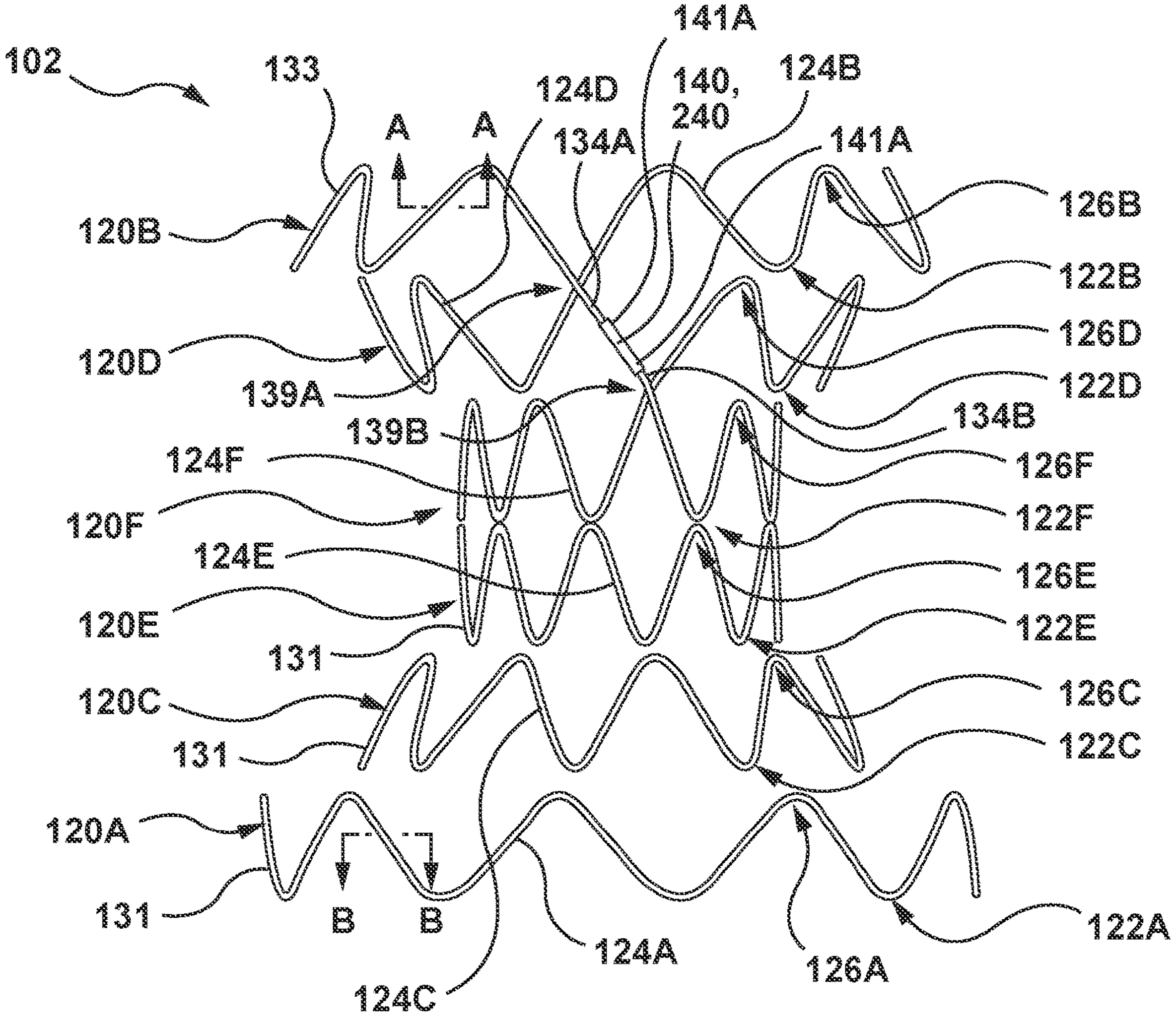
FIG. 5 is a side exploded view of a plurality of stents of the prosthetic valve device of FIG. 1.

FIG. 5 is a side exploded view of the frame 102 and depicts a side view of each of the inflow row 120A, the outflow row 120B, and the plurality of body rows 120C, 120D, 120E, 120F of the prosthetic valve device 100 in their radially expanded or deployed configuration prior to assembly, i.e., prior to attachment to the tubular graft 110 and attachment to each other. With reference to the exploded view of FIG. 5, each of the inflow row 120A, the outflow row 120B, and each row of the plurality of body rows 120C, 120D, 120E, 120F is a sinusoidal patterned radially-expandable ring having a first set of bends or crowns 122A, 122B, 122C, 122D, 122E, 122F (collectively referred to herein as the first set of crowns 122) and a second set of bends crowns 126A, 126B, 126C, 126D, 126E, 126F (collectively referred to herein as the second set of crowns 126), with a strut or straight segment 124A, 124B, 124C, 124D, 124E, 124F (collectively referred to herein as the struts 124) being formed between a pair of opposing crowns. Stated another way, each crown of the first and second sets of crowns 122, 126 is a curved segment or bend extending or formed between a pair of opposing struts 124. Collectively, the first set of crowns 122, the struts 124, and the second set of bends crowns 126 form or define the sinusoidal pattern of each row. The first set of crowns 122 opposes the second set of crowns 126, with the first set of crowns 122 being disposed closer to the inflow end 112 of the tubular graft 110 than the second set of crowns 126. The second set of crowns 126A, 126C, 126D, 126D, 126E, 126F of each of the inflow row 120A and each body row of the plurality of body rows 120C, 120D, 120E, 120F are disposed against and attached to the first set of crowns of an adjacent stent via stitching.

The first set of crowns 122A of the inflow row 120A may be considered endmost inflow crowns and are disposed at the inflow end of the frame 102. The number of endmost inflow crowns may vary according to size and application and may range, for example, between 6-15 crowns. In an embodiment, the inflow row 120A has a total of nine endmost inflow crowns, as best shown in the end view of FIG. 2. However, the configuration of the frame 102 is exemplary and other stent configurations are contemplated. Similarly, the second set of crowns 126B of the outflow row 120B may be considered endmost outflow crowns and are disposed at the outflow end of the frame 102. The number of endmost outflow crowns may also vary according to size and application and may range, for example, between 6-15 crowns. In an embodiment, the outflow row 120B has a total of nine endmost outflow crowns.

Each pair of adjacent rows 120 of the frame 102 are attached to each other in a crown-to-crown configuration. More particularly, the second set of crowns 126A, 126C, 126D, 126E, 126F of each of the inflow row 120A and each body row of the plurality of body rows 120C, 120D, 120E, 120F is disposed against and attached to the first set of crowns of the row directly adjacent thereto by a plurality of axial suture loops extending over adjacent crowns as shown in FIG. 1. More particularly, the second set of crowns 126A, 126C, 126D, 126E, 126F of each of the inflow row 120A and each body row of the plurality of body rows 120C, 120D, 120E, 120F is attached to the first set of crowns of an adjacent stent via stitching. Each pair of adjacent rows 120 are attached to each other with at least a pair of stitches that extend over the abutting crowns, in an axial direction. The second set of crowns 126A of the inflow row 120A is attached to the first set of crowns 122C of the first body row 120C, the second set of crowns 126C of the first body row 120C is attached to the first set of crowns 122E of the third body row 120E, the second set of crowns 126E of the third body row 120E is attached to the first set of crowns 122F of the fourth body row 120F, the second set of crowns 126F of the fourth body row 120F is attached to the first set of crowns 122D of the second body row 120D, and the second set of crowns 126D of the second body row 120D is attached to the first set of crowns 122B of the outflow row 120B.

As stated above, the frame 102 includes the first longitudinal portion 130 and the second longitudinal portion 132 which is disposed axially adjacent to the first longitudinal portion 130. The first longitudinal portion 130 is directly beside or adjacent to the second longitudinal portion 132, but the portions do not overlap or overlay. In the embodiment of FIGS. 1-6E, the first longitudinal portion 130 includes the inflow end 104 of the prosthetic valve device 100 and the second longitudinal portion 132 includes the outflow end 106 of the prosthesis. The first longitudinal portion 130 includes or forms rows 120A, 120C, 120E of the plurality of rows 120 and the second longitudinal portion includes or forms rows 120B, 120D, 120F less than a length of the second longitudinal portion 132, primarily due to the angle of flare of the inflow end 104. In another embodiment, a length of the first longitudinal portion 130 is substantially equal to a length of the second longitudinal portion 132. The prosthetic valve component 108 is disposed adjacent to a junction between the first longitudinal portion 130 and the second longitudinal portion 132. Although each of the first and second longitudinal portions 130, 132 includes three rows 120 in the embodiment of FIGS. 1-6E, other embodiments are contemplated. For example, in another embodiment, each of the first and second longitudinal portions 130, 132 includes or forms between two and five rows. Each of the first and second longitudinal portions 130, 132 preferably include at least two rows 120, but the first and second longitudinal portions 130, 132 are not required to include the same number of rows.

Figure 5A:
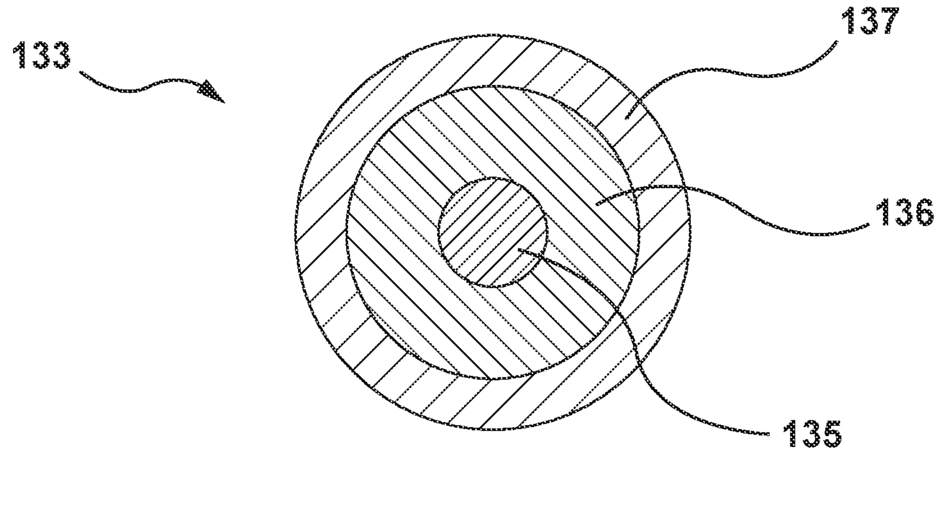
FIG. 5A is a cross-sectional view taken along line A-A of FIG. 5.
Figure 5B:
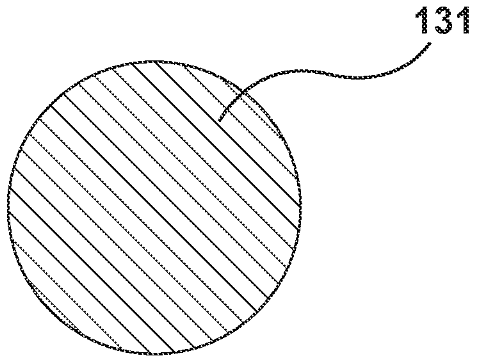
FIG. 5B is a cross-sectional view taken along line B-B of FIG. 5.

In the embodiment of FIGS. 1-6E, as best shown on the exploded view of FIG. 5, each row 120A, 120C, 120E of the first longitudinal portion 130 is formed from an individual or separate stent. Each stent forming one of the rows 120A, 120C, 120E is manufactured or formed in its radially expanded or deployed configuration and is constructed from a solid wire 131 that is shaped into a sinusoidal patterned ring. Each row 120A, 120C, 120E of the first longitudinal portion 130 is formed from the wire 131 of a relatively strong, self-expanding material. In an embodiment, each row of the first longitudinal portion 130 is constructed from a self-expanding or spring material, including but not limited to nickel titanium alloys such as Nitinol™. FIG. 5B illustrates a cross-sectional view taken along line B-B of FIG. 5, through the wire 131 forming the inflow row 120A. As shown, the wire 131 may have a circular cross-section.

Although the first longitudinal portion 130 is depicted as being formed from three individual or separate stents via a solid wire, in another embodiment hereof (not shown), one or more of the rows 120A, 120C, 120E may be cut from tubing and shape set into the desired configuration, with adjacent stents being subsequently sutured or otherwise attached to each other at abutting crowns. Further, in another embodiment hereof (not shown), all rows 120A, 120C, 120E may be constructed as a unitary component that is cut from tubing and shape set in the desired configuration.

The second longitudinal portion 132 is formed from a single elongated composite wire 133 having a first end 134A and a second end 134B opposing the first end. FIG. 5A illustrates a cross-sectional view taken along line A-A of FIG. 5, through the composite wire 133. The composite wire 133 includes a core 135 of a first material, an intermediate layer 136 of a second material, and an outer layer 137 of a third material. The first material is an electrically conductive material, such as platinum, copper, gold, nickel, aluminum, silver, and the like. The second material is a self-expanding or spring material, including but not limited to nickel titanium alloys such as Nitinol™. The third material is an electrically insulative material such as but not limited to Parylene. In an embodiment, the first material is platinum, the second material is Nitinol, and the third material is Parylene.

Figure 6A:
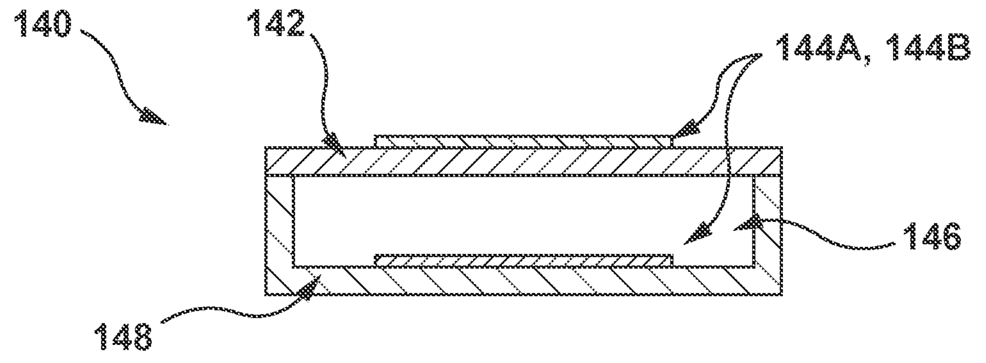
FIG. 6A is a side view of an embodiment of a sensor suitable for use on the prosthetic valve device of FIG. 1, the sensor including a membrane/diaphragm.
Figure 6B:
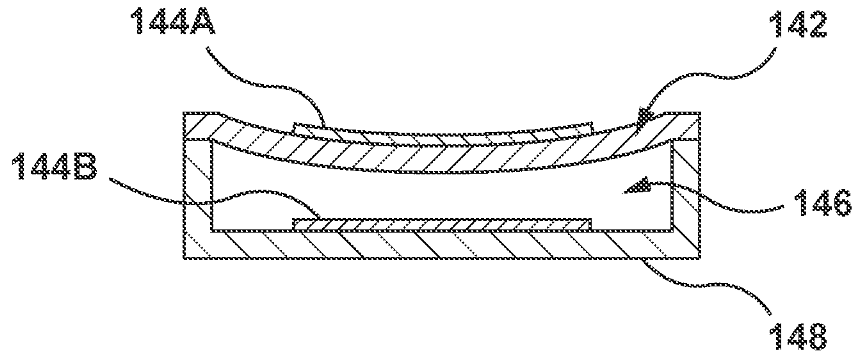
FIG. 6B is a side view of the sensor of FIG. 6B with the membrane deformed.
Figure 6C:
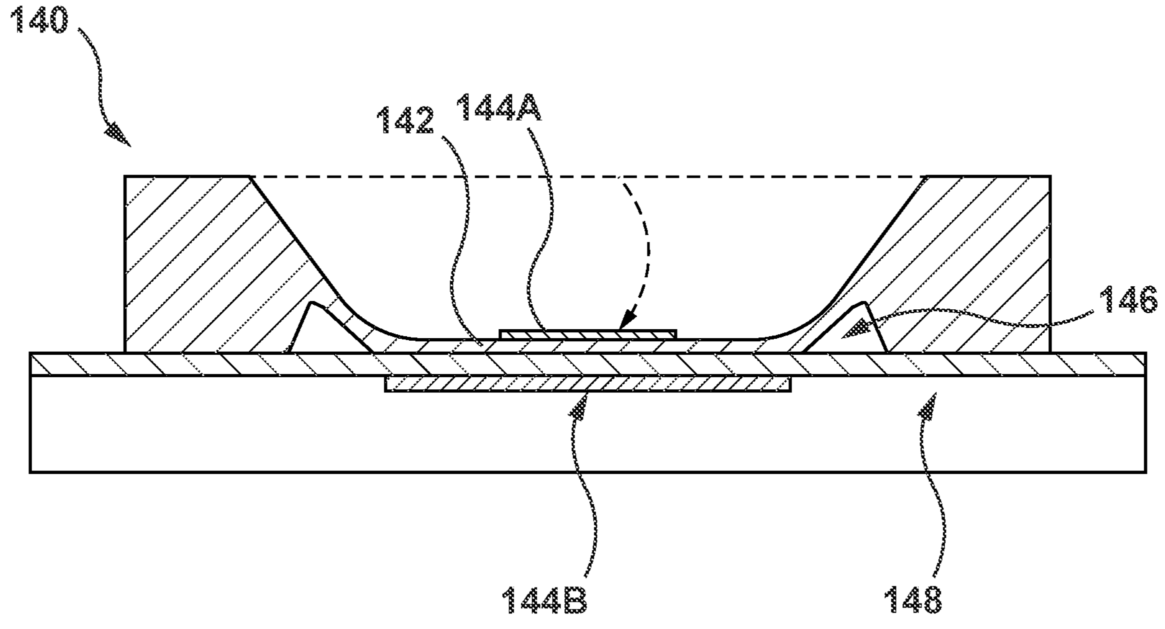
FIG. 6C is a schematic diagram of the sensor of FIG. 6A illustrating the deformable nature of the membrane.
Figure 6D:
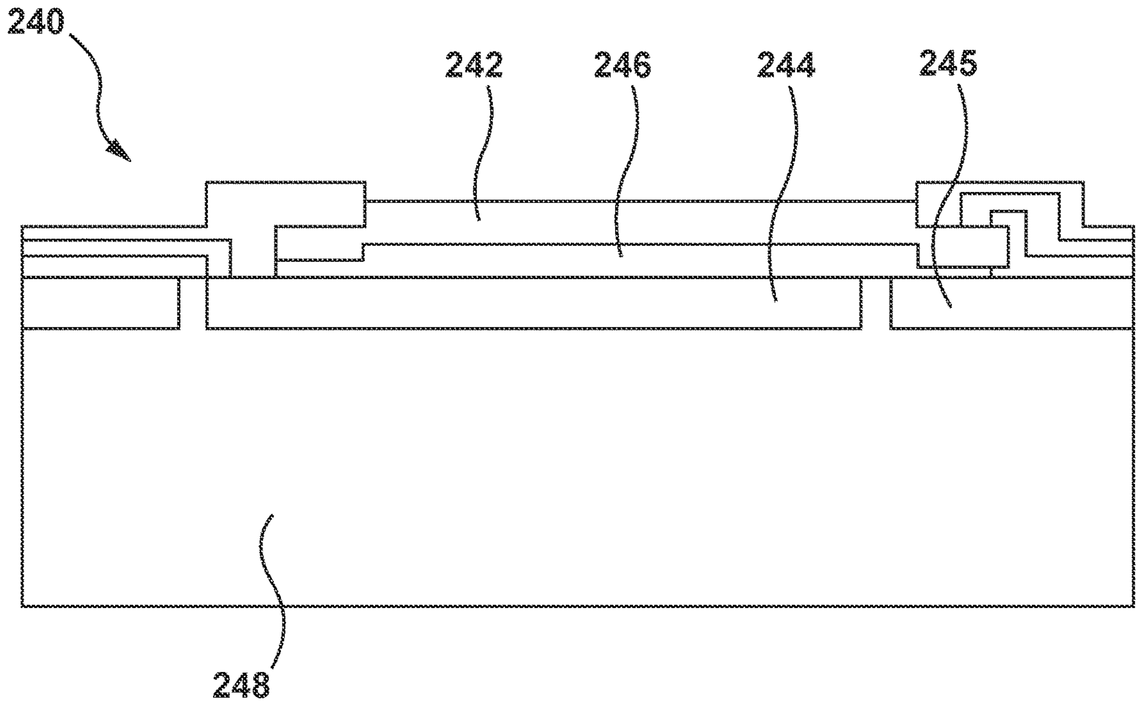
FIG. 6D is a side view of another embodiment of a sensor suitable for use on the prosthetic valve device of FIG. 1.
Figure 6E:
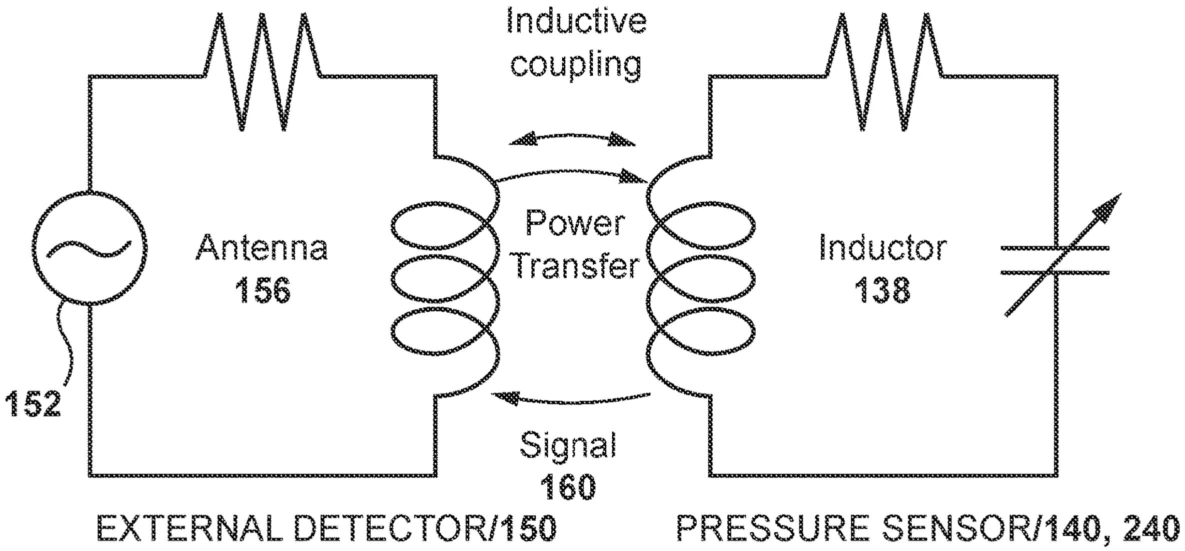
FIG. 6E is a schematic diagram of the prosthetic valve device of FIG. 1 in communication with an external detector.

As best shown on FIG. 5, a first end 141A of the sensor 140, 240 is attached to the first end 134A of the composite wire 133 and a second end 141B of the sensor 140, 240 is attached to the second end 134B of the composite wire 133. FIGS. 6A-6C illustrate the sensor 140 in more detail, while FIG. 6E illustrates the sensor 240 in more detail. In the embodiment of FIGS. 6A-6C, the first end 134A of the composite wire 133 would be in electrical communication with one of a first electrode 144A or a second electrode 144B, and the second end 134B of the composite wire 133 would be in electrical communication with the other of the first electrode 144A and the second electrode 144B (i.e., the electrode 144A, 144B that is not in electrical communication with the first end 134A). In the embodiment of FIG. 6D, the first end 134A of the composite wire 133 would be in electrical communication with one of a flexible membrane or diaphragm 242 or an electrode 244, and the second end 134B of the composite wire 133 would be in electrical communication with the other of the diaphragm 242 or the electrode 244. The ends 141A, 141B of the sensor 140, 240 may be attached to the ends 134A, 134B of the composite wire 133 via any suitable manner that ensures the composite wire 133 is in electrical communication with the sensor 140, 240. For example, the ends 141A, 141B of the sensor 140, 240 may be attached to the ends 134A, 134B of the composite wire 133 via welding, a crimp tube, electrically conductive adhesives, or other suitable fastener. Connection via a crimp tube (not shown) also may serve to increase the strength of the composite wire 133 at an end 134A, 134B thereof, as the ends 134A, 134B may be a low stress concentration area which is prone to breakage.

The second longitudinal portion 132 forms the inductor 138 that is in electrical communication with the sensor 140, 240 and is configured to relay or output a signal or frequency 160, which is associated with the sensor 140, 240, to be received by an external detector 150 as described in more detail below with respect to FIGS. 12-13. To function as the inductor 138, the composite wire 133 winds or spirals into a coiled stent having a plurality of windings, i.e., each row 120B, 120D, 120F of the plurality of rows 120 is a winding of the coiled stent. Since the coiled stent includes three windings or rows, the composite wire 133 overlaps or overlays itself (or the sensor 140, 240) at two locations 139A, 139B. However, since the composite wire 133 includes the outer layer 137 of an electrically insulative material, the core 135 of the composite wire 133 does not come into contact with itself at the two locations 139A, 139B to preserve the function of the inductor 138. The overlapping portions of the composite wire 133 at the two locations 139A, 139B may be secured to each other via sutures and/or polymer adhesive.

The sensor 140, 240 is configured to measure a flow parameter within the prosthetic valve device 100. The sensor 140, 240 may be a flexible pressure sensor configured to measure external pressure(s) caused by forces such as compression applied to the sensor 140, 240. The sensor 140, 240 is configured to convert capacitance into an electrical signal using four essential components: a flexible member, at least one electrode, a cavity, and a dielectric layer/substrate. The sensor 140 of FIGS. 6A-6C is a passive capacitive pressure sensor including a flexible member or diaphragm 142, the first electrode 144A which is disposed on the diaphragm 142, and the second electrode 144B which is disposed on a base layer or substrate 148. More particularly, the base layer or substrate 148 may be a dielectric layer for the storage of charge. The diaphragm 142 and base layer 148 are separated from each other by some distance so as to create separation between the first electrode 144A and the second electrode 144B. Disposed between the first and second electrodes 144A, 144B is a cavity 146 through which the diaphragm 142 may translate, bend, collapse, deform, or otherwise move through/into. As the diaphragm 142 deforms into the cavity 146, the distance between the first and second electrodes 144A, 144B decreases, thus altering the capacitance of the sensor 140. FIG. 6C illustrates a schematic diagram of the relationship between the diaphragm 142 and the second electrode 144B or base layer/substrate 148 of the embodiment of the passive capacitive pressure sensor 140. As shown in FIGS. 6B and 6C, the flexible member or diaphragm 142 is capable of bending, translating, deforming, or moving through the entirety of the cavity 146 such that the diaphragm 142 and the first electrode 144A may become adjacent to or in contact with the second electrode 144B and/or the base layer 148. The diaphragm 142 may be composed of materials such as plastic, glass, silicon, or ceramic, for example.

In operation, the sensor 140 is configured to measure pressure by detecting changes in electrical capacitance (i.e., the ability to store electric charge) caused by movement of the diaphragm 142 through the cavity 146. The pressure within the space of the cavity 146 may be a vacuum, or more particularly an absolute pressure (i.e., perfect vacuum), or a relative pressure (i.e., atmospheric pressure corrected to sea-level conditions). When pressure is applied to the diaphragm 142, the diaphragm 142 and first electrode 144A move through the cavity 146 towards the second electrode 144B, thus reducing the distance between the diaphragm 142 and the second electrode 144B and reducing the size of the cavity 146. When the applied pressure is reduced or removed, the diaphragm 142 and first electrode 144A move through the cavity 146 away from the second electrode 144B, thus increasing the distance between the diaphragm 142 and the second electrode 144B and increasing the size of the cavity 146. The amount of pressure being applied at any given time varies, resulting in up and down or wobbling movement of the diaphragm 142. The diaphragm 142 moves between a neutral state in which no pressure is applied thereto (as exemplified in FIG. 6A, and further illustrated by the phantom line in FIG. 6C) and a bending state (as exemplified in 6B, and further illustrated by the phantom arrow in FIG. 6C). The movement of the diaphragm 142 between these states reduces or increases the distance between the first electrode 144A and the second electrode 144B, resulting in an increase or decrease in electrical capacitance relative to a distance between the first electrode 144A and the second electrode 144B. When the size of the cavity 146 is reduced due to movement of the diaphragm 142, the capacity or capacitance of the sensor 140 decreases. Similarly, when the size of the cavity 146 is increased due to movement of the diaphragm 142, the capacity or capacitance of the sensor 140 increases. Stated another way, the electrical capacitance of the sensor 140 changes or varies as a result of movement of the diaphragm 142. This increase/decrease in electrical capacitance may be received by an integrated circuit (not shown), which may be an oscillator or a resonant circuit, an LC circuit, a tank circuit, or a tuned circuit, for example. This change in capacitance results in a change in frequency which is then generated as a signal or frequency 160 relative to the provided increase/decrease in electrical capacitance as further described herein.

The sensor 240 of FIG. 6D is a passive capacitive pressure sensor and includes a diaphragm 242, a conducting plate 244, a cavity 246 disposed between the diaphragm 242 and the conducting plate 244, a substrate 248 for supporting the diaphragm 242 and conductive plate 244, and an integrated circuit 245. Due to its passive nature, the sensor 240 may be wireless and/or battery-less. The sensor 240 may be between 1 to 500 microns in size. In an embodiment, the sensor 240 is a flexible sensor, for example a thin film flexible sensor made using microelectromechanical systems (MEMS) techniques typically used for the creation of integrated devices that incorporate a combination of mechanical and electrical components. The flexible sensor is composed of deposited electrodes and dielectric layers with polymer insulation packaging. In another embodiment, the sensor 240 is a rigid sensor, for example a capacitive sensor composed of a diaphragm and substrate composed of ceramic packaging material, i.e., aluminum oxynitride, magnesium aluminate spinel, or single crystal aluminum oxide (also known as sapphire ceramic). In this embodiment, the rigid sensor incorporates conductive components such as metal electrodes (i.e., electrodes composed of copper, graphite, titanium, brass, silver, or platinum; the electrodes being similar to those presented in FIGS. 6A-6C) with the ceramic packaging material to achieve increased reliability and stability of the sensor structure. The sensor 240 may be a commercially available pressure sensor available from Murata Manufacturing Co. of Nagaokakyo, Japan.

In operation, the sensor 240 is configured to measure pressure by detecting changes in electrical capacitance (i.e., the ability to store electric charge) caused by the movement of the diaphragm 242. The diaphragm 242 may be flexible, and composed of materials such as plastic, glass, silicon, or ceramic, for example. When pressure is applied to the diaphragm 242, the diaphragm 242 moves through the cavity 246 toward the conducting plate 244, thus reducing the distance between the diaphragm 242 and the conducting plate 244 and reducing the size of the cavity 246. When the applied pressure is reduced or removed, the diaphragm 242 moves through the cavity 246 away from the conducting plate 244, thus increasing the distance between the diaphragm 242 and the conducting plate 244 and increasing the size of the cavity 246. The amount of pressure being applied at any given time varies, resulting in a wobbling effect or movement of the diaphragm 242. When the size of the cavity 246 is reduced due to movement of the diaphragm 242, the capacity or capacitance of the sensor 240 decreases. Similarly, when the size of the cavity 246 is increased due to movement of the diaphragm 242, the capacity or capacitance of the sensor 240 increases. Stated another way, the electrical capacitance of the sensor 240 changes or varies as a result of movement of the diaphragm 242. The increase/decrease in electrical capacitance is received by the integrated circuit 245, which may be an oscillator or a resonant circuit, an LC circuit, a tank circuit, or a tuned circuit, for example. Upon receiving this change in capacitance, the integrated circuit 245 will experience a change in frequency generated as the signal or frequency 160 relative to the provided increase/decrease in electrical capacitance.

FIG. 6E shows an exemplary circuit formed via the sensor 140, 240 and the inductor 138. The inductor 138, formed by the coiled stent of the second longitudinal portion 132 as described above, generates an inductance L, or a change in electrical current therein. When the sensor 140, 240 experiences an increase or decrease in capacitance due to forces applied against the diaphragm 142 as previously described herein, the frequency of the integrated circuit 145 changes, which in turn generates the inductance L of the inductor 138 resulting in an output of the signal or frequency 160. The signal or frequency 160 relayed or output by the inductor 138 is intercepted, detected, or otherwise received by an antenna 156 of the external detector 150, which includes a waveform generator or vector network analyzer 152 as further described herein. The waveform generator 152 may include an integrated GUI 158. The signal or frequency 160 of the inductor 138 is transmitted to the external detector 150 through inductive coupling, such that the signal 160 emitted from the inductor 138 creates interference or inductance with the external detector 150. When received by the external detector 150, the signal or frequency 160 is converted or otherwise processed to a measurement of instantaneous blood pressure. The sensor 140, 240 may thus be considered to be configured to measure a flow parameter indicative of the fluid pressure generated by blood or bodily fluid flowing through the prosthetic valve device 100 and over the sensor 140, 240. The external detector 150 further performs as a powering device, such that placing the external device 150 within a specific location/orientation close to the sensor 140, 240, then powering on the external device 150 (i.e., powering on the waveform generator 152), will initiate inductive coupling between the antenna 156 and the inductor 138 and begin a power transfer, as illustrated by the arrow in FIG. 6E. The external detector 150 is described in greater detail below with respect to FIGS. 12-13.

In the embodiment of FIGS. 1-6E, the inductor 138 is advantageously formed via the second longitudinal portion 132 which includes the outflow end 106 of the prosthetic valve device 100 because the outflow end 106 is believed to be subjected to less strain in vivo than the first longitudinal portion 130. Since the composite wire 133 includes the electrically conductive core 135, the strength of the composite wire 133 which forms the coiled stent of the second longitudinal portion 132 is less than the strength of the solid wire 131 which forms each stent of the first longitudinal portion 130. Thus, in the embodiment of FIGS. 1-6E, the first longitudinal portion 130 is relatively stronger than the second longitudinal portion 132 to account for the inflow end 104 (of the first longitudinal portion 130) being subjected to higher strain in vivo.

Although a single sensor 140, 240 is depicted in the embodiment of FIGS. 1-6E for measuring the flow parameter, the prosthetic valve device 100 may include a plurality of sensors 140, 240 electrically coupled to the inductor 138 for measuring the flow parameter. Each sensor 140, 240 of the plurality of sensors is in electrical communication with the inductor 138. Redundancy in the number of sensors 140, 240 ensures more reliable measurement of the flow parameter, and more reliable signal receiving by the external detector 150. Having multiple sensors with varying degrees of anti-fouling prevention allows the prosthetic valve device 100 to switch to a better functioning sensor if or when a first sensor gets fouled. For example, in an embodiment, between two and nine sensors 140, 240 may be electrically coupled the inductor 138. Since each sensor 140, 240 is very small in size, incorporation of multiple sensors 140, 240 on the inductor 138 does not significantly increase the profile of the inductor 138.

Figure 7:
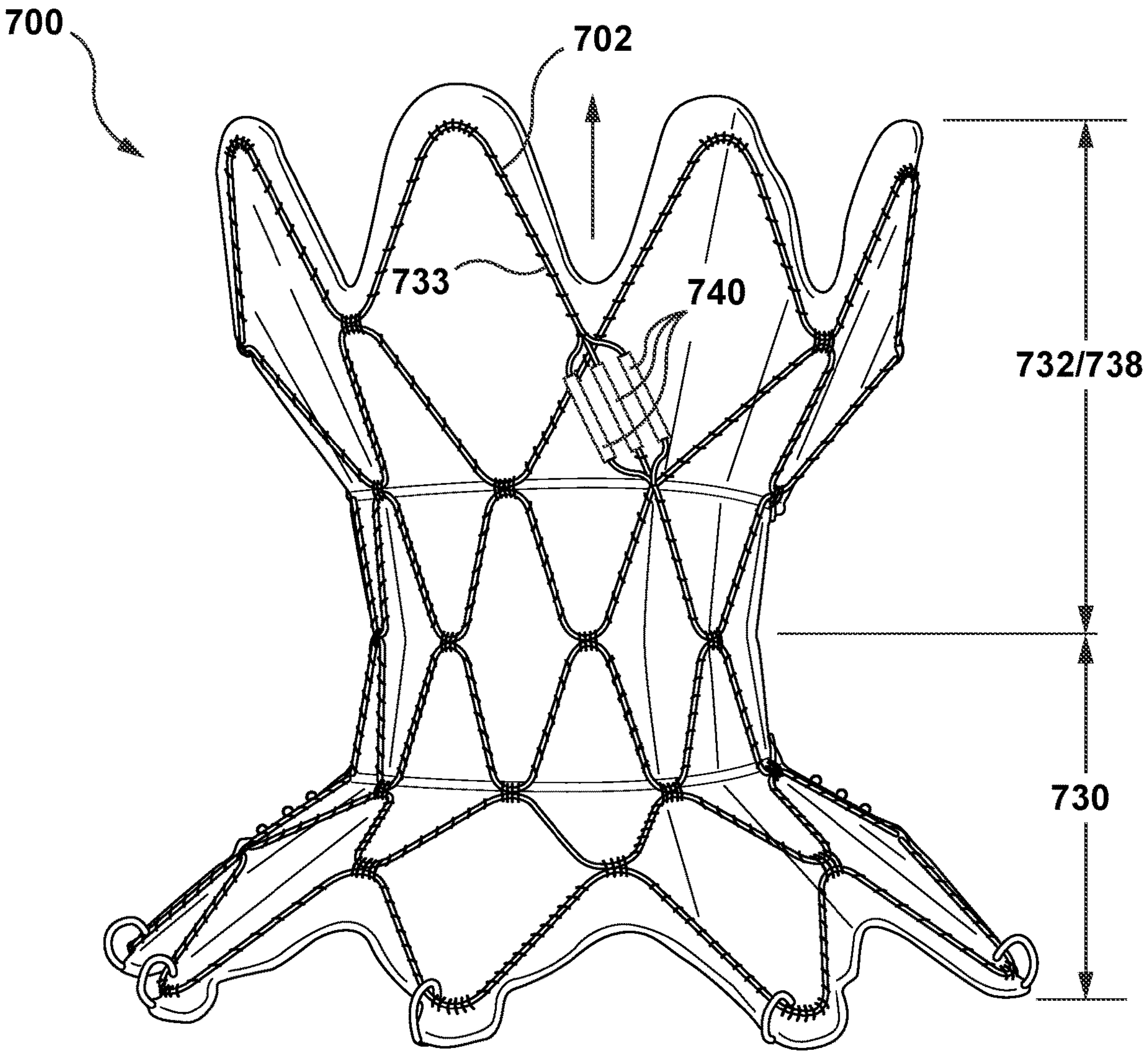
FIG. 7 is a side view of a prosthetic valve device according to another aspect of the present disclosure, wherein the prosthetic valve device is shown in its radially expanded or deployed configuration, and wherein the prosthetic valve device includes a first sensor in electrical communication with a first inductor formed by a first stent of the prosthetic valve device.

More particularly, FIG. 7 illustrates an embodiment in which the prosthetic valve device includes a plurality of sensors in electrical communication with the same inductor to achieve more reliable signal output and reception. More particularly, FIG. 7 depicts a prosthetic valve device 700 with a frame 702 including a first longitudinal portion 730 and a second longitudinal portion 732 which is disposed axially adjacent to the first longitudinal portion 730. The first longitudinal portion 730 is the same as the first longitudinal portion 130 described above, and thus the details hereof are not repeated herein for sake of brevity. The second longitudinal portion 732 is similar to the second longitudinal portion 132 described above in that it includes a single elongated composite wire 733, which is the same as the single elongated composite wire 133 described above. However, rather than a single sensor connected to the composite wire 133, the second longitudinal portion 732 includes a plurality of sensors 740 connected to the composite wire 733. More particularly, three sensors 740 are connected to the composite wire 733. Each of the three sensors 740 is illustrated in FIG. 7 as being connected to the composite wire 733 in parallel, however in embodiments the three sensors 740 may alternatively be connected to the composite wire 733 in series (not shown). It should further be understood that the number of sensors 740 connected in parallel or series to the composite wire 733 is not limited to three, as shown in FIG. 7. In embodiments, two, three, four, five, six, seven, or more sensors 740 may be connected in parallel or in series to the composite wire 733. Similar to the previous embodiment of FIGS. 1-6E, the second longitudinal portion 732 forms an inductor 738 that is in electrical communication with the plurality of sensors 740 and is configured to relay or output a signal or frequency, which is associated with the plurality of sensors 740, to be received by an external detector. Each sensor 740 may be one of the sensors 140, 240 described above.

Figure 8:
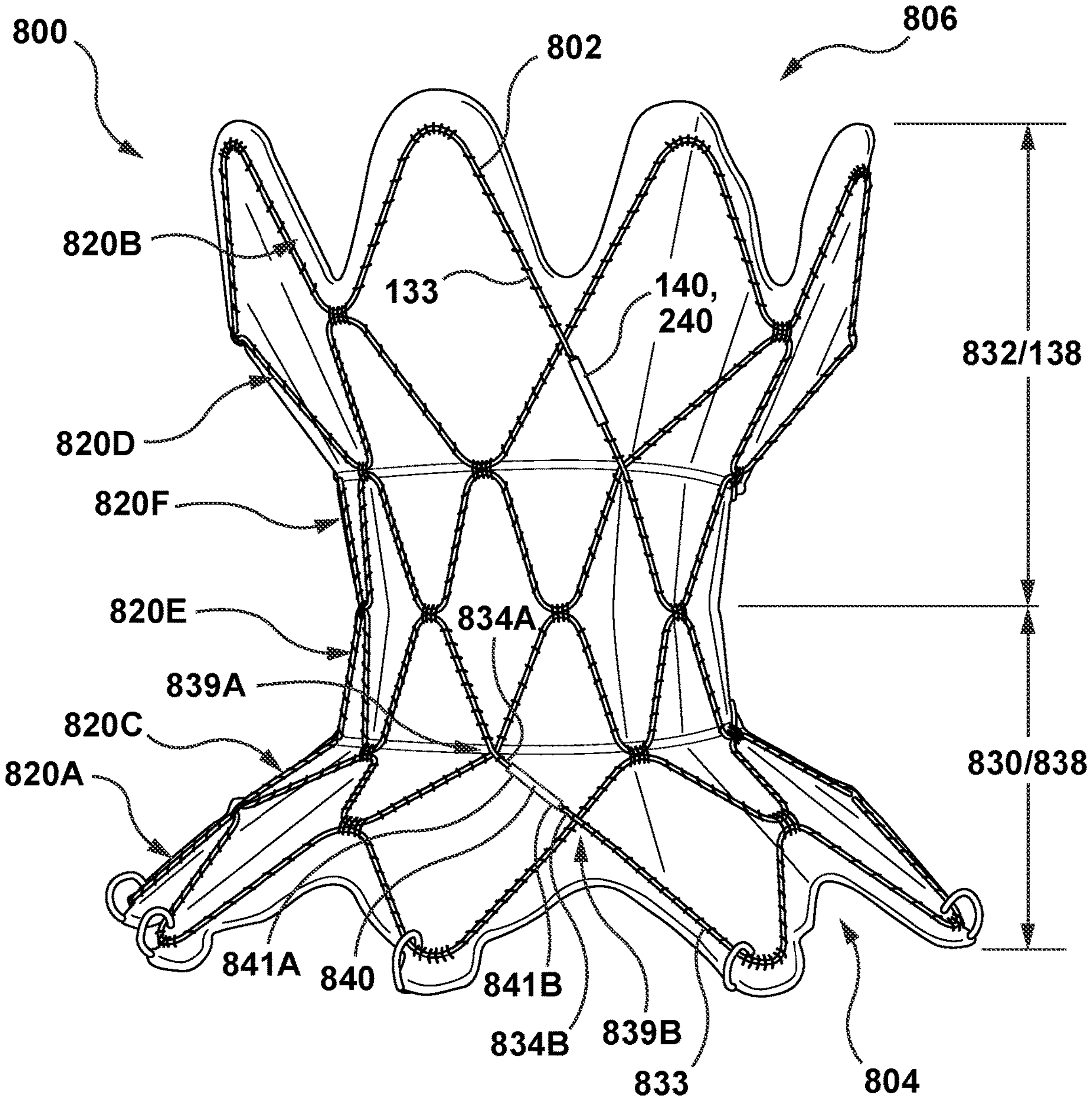
FIG. 8 is a side view of a prosthetic valve device according to another aspect of the present disclosure, wherein the prosthetic valve device is shown in its radially expanded or deployed configuration, and wherein the prosthetic valve device includes a first sensor in electrical communication with a first inductor formed by a first stent of the prosthetic valve device and a second sensor in electrical communication with a second inductor formed by a second stent of the prosthetic valve device.

In another embodiment hereof, the first longitudinal portion of the prosthetic valve device may form a second inductor such that pressure measurements at the inflow and outflow ends of the prosthetic valve device may be monitored, thereby enabling gradient (i.e., blood flow rate) calculations. More particularly, FIG. 8 depicts a prosthetic valve device 800 with a frame 802 including a first longitudinal portion 830 and a second longitudinal portion 832 which is disposed axially adjacent to the first longitudinal portion 830. The first longitudinal portion 830 is directly beside or adjacent to the second longitudinal portion 832, but the portions do not overlap or overlay. In the embodiment of FIG. 8, the first longitudinal portion 830 includes an inflow end 804 of the prosthetic valve device 800 and the second longitudinal portion 832 includes an outflow end 806 of the prosthesis. The first longitudinal portion 830 includes or forms rows 820A, 820C, 820E of a plurality of rows 820 and the second longitudinal portion includes or forms rows 820B, 820D, 820F of the plurality of rows 820.

The second longitudinal portion 832 is the same as the second longitudinal portion 132 described above and includes the single elongated composite wire 133 and the sensor 140, 240, which may be considered a first sensor in this embodiment. The second longitudinal portion 832 forms the inductor 138, which may be considered a first inductor in this embodiment, that is in electrical communication with the first sensor 140, 240 and is configured to relay or output a signal or frequency, which is associated with the first sensor 140, 240, to be received by an external detector as described above with respect to FIGS. 1-6E.

In this embodiment, the first longitudinal portion 830 is also formed from a single elongated composite wire 833 and includes a sensor 840, which is the same as the sensor 140, 240 described above and may be considered a second sensor in this embodiment. The first longitudinal portion 830 forms an inductor 838, which may be considered a second inductor in this embodiment. The composite wire 833 has a first end 834A and a second end 834B opposing the first end. The composite wire 833 is the same construction as the composite wire 133 and includes the core 135 of a first material, the intermediate layer 136 of a second material, and the outer layer 137 of a third material. A first end 841A of the second sensor 840 is attached to the first end 834A of the composite wire 833 and a second end 841B of the second sensor 840 is attached to the second end 834B of the composite wire 833.

The first longitudinal portion 830 forms the second inductor 838 that is in electrical communication with the second sensor 840 and is configured to relay or output a signal or frequency, which is associated with the sensor 840, to be received by an external detector. To function as the second inductor 838, the composite wire 833 winds or spirals into a coiled stent having a plurality of windings, i.e., each row 820A, 820C, 820E of the plurality of rows 820 is a winding of the coiled stent. Since the coiled stent includes three windings or rows, the composite wire 833 overlaps or overlays itself (or the sensor 840) at two locations 839A, 839B. However, since the composite wire 833 includes the outer layer 137 of an electrically insulative material, the core 135 of the composite wire 833 does not come into contact with itself at the two locations 839A, 839B as to not interfere with the operation or function of the second inductor 838. The overlapping portions of the composite wire 833 at the two locations 839A, 839B may be secured to each other via sutures and/or polymer adhesive.

The second inductor 838, formed by the coiled stent of the first longitudinal portion 830 as described above, generates an inductance L, or a change in electrical current therein. When the second sensor 840 experiences an increase or decrease in capacitance due to forces applied against the diaphragm as previously described herein with respect to the sensor 140, 240, the frequency of the integrated circuit changes, which in turn generates the inductance L of the second inductor 838 resulting in an output of the signal or frequency. The signal or frequency relayed or output by the second inductor 838 is intercepted, detected, or otherwise received by the external detector. The signal or frequency of the second inductor 838 is transmitted to the external detector through inductive coupling, such that the signal emitted from the second inductor 838 creates interference or inductance with the external detector.

The prosthetic valve device 800 thus includes the second sensor 840, in electrical communication with the second inductor 838, disposed at the inflow end 804 of the prosthetic valve device 800 and the first sensor 140, 240, in electrical communication with the first inductor 138, disposed at the outflow end 806 of the prosthetic valve device 800. Stated another way, the second sensor 840 is disposed closer to the inflow end 804 of the prosthetic valve device 800 and the first sensor 140, 240 is disposed closer to the outflow end 806 of the prosthetic valve device 800. By arranging the first sensor 140, 240 and the second sensor 840 in this manner, or in similar configurations where the first sensor 140, 240 and the second sensor 840 are separated from each other by a longitudinal distance, a gradient flow parameter (i.e., blood flow rate) may be measured between the first sensor 140, 240 and the second sensor 840, or a measured increase or decrease in blood pressure caused by the flowing fluid. More particularly, the flow parameter measured may be a gradient indicating a rise or drop in blood pressure between certain points on the prosthetic valve device 800 represented by the locations of the first sensor 140, 240 and the second sensor 840.

Figure 9:
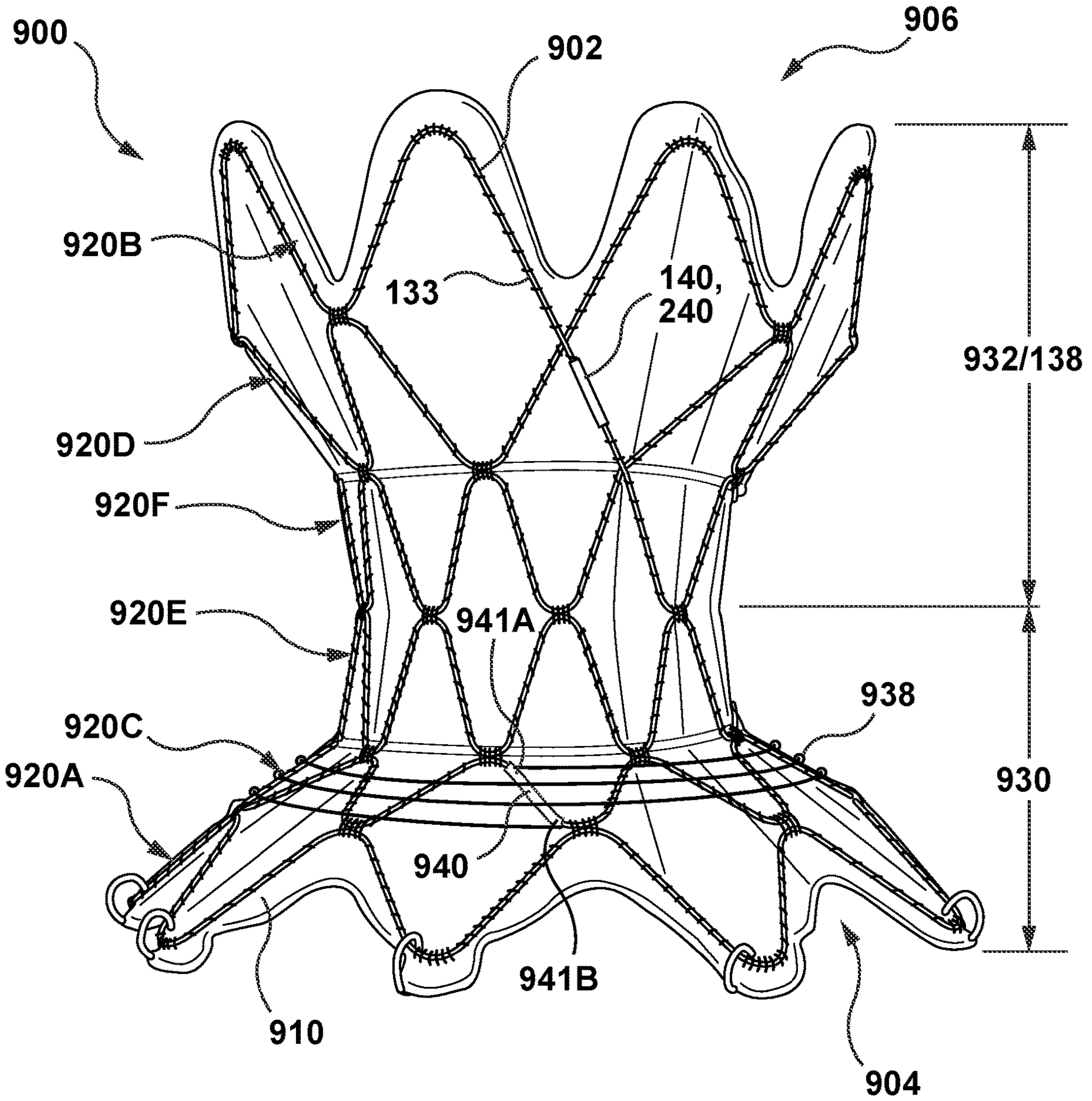
FIG. 9 is a side view of a prosthetic valve device according to another aspect of the present disclosure, wherein the prosthetic valve device is shown in its radially expanded or deployed configuration, and wherein the prosthetic valve device includes a first sensor in electrical communication with a first inductor formed by a first stent of the prosthetic valve device and a second sensor in electrical communication with a second inductor coupled to the prosthetic valve device.

Another embodiment hereof is depicted in FIG. 9, in which the first longitudinal portion of the prosthetic valve device has a second inductor coupled thereto such that pressure measurements at the inflow and outflow ends of the prosthetic valve device may be monitored, thereby enabling gradient calculations. More particularly, FIG. 9 depicts a prosthetic valve device 900 with a frame 902 including a first longitudinal portion 930 and a second longitudinal portion 932 which is disposed axially adjacent to the first longitudinal portion 930. The first longitudinal portion 930 is directly beside or adjacent to the second longitudinal portion 932, but the portions do not overlap or overlay. In the embodiment of FIG. 9, the first longitudinal portion 930 includes an inflow end 904 of the prosthetic valve device 900 and the second longitudinal portion 932 includes an outflow end 906 of the prosthesis. The first longitudinal portion 930 includes or forms rows 920A, 920C, 920E of a plurality of rows 920 and the second longitudinal portion includes or forms rows 920B, 920D, 920F of the plurality of rows 920.

The second longitudinal portion 932 is the same as the second longitudinal portion 132 described above and includes the single elongated composite wire 133 and the sensor 140, 240, which may be considered a first sensor in this embodiment. The second longitudinal portion 932 forms the inductor 138, which may be considered a first inductor in this embodiment, that is in electrical communication with the first sensor 140, 240 and is configured to relay or output a signal or frequency, which is associated with the first sensor 140, 240, to be received by an external detector as described above with respect to FIGS. 1-6E.

Similar to the first longitudinal portion 130, the first longitudinal portion 930 includes rows 920A, 920C, 920E each of which is formed from an individual or separate stent. Each stent forming one of the rows 920A, 920C, 920E is manufactured or formed in its radially expanded or deployed configuration and is constructed from a wire that is shaped into a sinusoidal patterned ring. Each row 920A, 920C, 920E of the first longitudinal portion 930 is formed from a solid wire of a relatively strong, self-expanding material. In an embodiment, each row of the first longitudinal portion 930 is constructed from a self-expanding or spring material, including but not limited to nickel titanium alloys such as Nitinol™.

The first longitudinal portion 932 also includes a sensor 940, which is the same as the sensor 140, 240 described above and may be considered a second sensor in this embodiment, and an inductor 938, which may be considered a second inductor in this embodiment. The sensor 940 is shown attached to and overlaying a strut of the first body row 920C, but this placement is exemplary. The sensor 940 may be attached to any portion of the frame 902 and/or the tubular graft 910.

Rather than being formed by a portion of the frame 902, the second inductor 938 is a coil having a plurality of windings coupled to the first longitudinal portion 932 of the frame 902. A first end of the coil/second inductor 938 is attached to a first end 941A of the sensor 940 and a second end of the coil/second inductor 938 is attached to a second end 941B of the sensor 940. The second inductor 938 is in electrical communication with the second sensor 940 and is configured to relay or output a signal or frequency, which is associated with the sensor 940, to be received by an external detector. In the depicted embodiment, the second inductor 938 encircles and is coupled to the first body row 920C of the first longitudinal portion 932 but may additionally and/or alternatively encircle the inflow row 920A and/or the third body row 920C. In an embodiment, the second conductor 938 is woven or braided through a tubular graft 910 of the prosthetic valve device 900 in order to be coupled thereto. More particularly, a flexible strand of electrically conductive material may be woven into the material of the tubular graft 910 in a coil shape or pattern to form the second inductor 938. In an embodiment, the strand of electrically conductive material may be stainless steel coated with a polymer such as Paralyne for insulation. In another embodiment, the strand of electrically conductive material may be platinum, copper, gold, nickel, aluminum, silver, and the like. Further, as an alternative to being woven into the tubular graft 910, the second inductor 938 may be secured to the tubular graft 910 and/or the stent forming one of the rows 920A, 920C, 920E via sutures, adhesive, and the like.

The second inductor 938 generates an inductance L, or a change in electrical current therein. When the second sensor 940 experiences an increase or decrease in capacitance due to forces applied against the diaphragm as previously described herein with respect to the sensor 140, 240, the frequency of the integrated circuit changes, which in turn generates the inductance L of the second inductor 938 resulting in an output of the signal or frequency. The signal or frequency relayed or output by the second inductor 938 is intercepted, detected, or otherwise received by the external detector. The signal or frequency of the second inductor 938 is transmitted to the external detector through inductive coupling, such that the signal emitted from the second inductor 938 creates interference or inductance with the external detector.

The prosthetic valve device 900 thus includes the second sensor 940, in electrical communication with the second inductor 938, disposed at the inflow end 904 of the prosthetic valve device 900 and the first sensor 140, 240, in electrical communication with the first inductor 138, disposed at the outflow end 906 of the prosthetic valve device 900. Stated another way, the second sensor 940 is disposed closer to the inflow end 904 of the prosthetic valve device 900 and the first sensor 140, 240 is disposed closer to the outflow end 906 of the prosthetic valve device 900. By arranging the first sensor 140, 240 and the second sensor 940 in this manner, or in similar configurations where the first sensor 140, 240 and the second sensor 940 are separated from each other by a longitudinal distance, a gradient flow parameter (i.e., blood flow rate) may be measured between the first sensor 140, 240 and the second sensor 940, or a measured increase or decrease in pressure caused by the flowing fluid. More particularly, the flow parameter measured may be a gradient indicating a rise or drop in blood pressure between certain points on the prosthetic valve device 900 represented by the locations of the first sensor 140, 240 and the second sensor 940.

In the embodiment of FIG. 9, the first inductor 138 is advantageously formed via the second longitudinal portion 932 which includes the outflow end 906 of the prosthetic valve device 900 because the outflow end 906 is believed to be subjected to less strain in vivo than the first longitudinal portion 930. Since the composite wire 133 includes the electrically conductive core 135, the strength of the composite wire 133 which forms the coiled stent of the second longitudinal portion 932 is less than the strength of the solid wire which forms each stent of the first longitudinal portion 930. Thus, in the embodiment of FIG. 9, the first longitudinal portion 930 is relatively stronger than the second longitudinal portion 932 to account for the inflow end 904 (of the first longitudinal portion 930) being subjected to higher strain in vivo.

Figure 10:
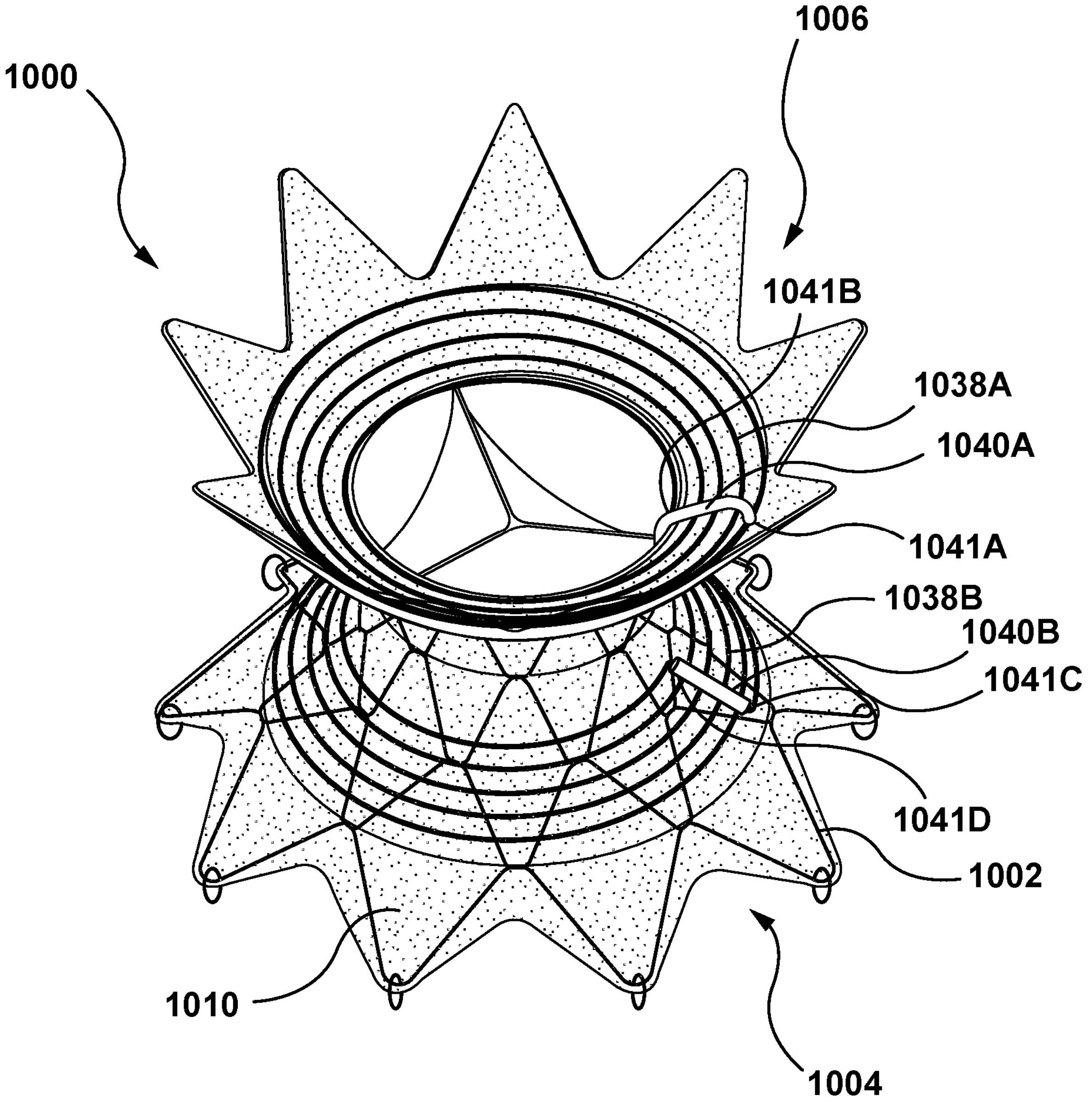
FIG. 10 is a perspective view of a prosthetic valve device according to another aspect of the present disclosure, wherein the prosthetic valve device is shown in its radially expanded or deployed configuration, and wherein the prosthetic valve device includes a first sensor in electrical communication with a first inductor coupled to the prosthetic valve device and a second sensor in electrical communication with a second inductor formed by a second stent of the prosthetic valve device.
Figure 11:
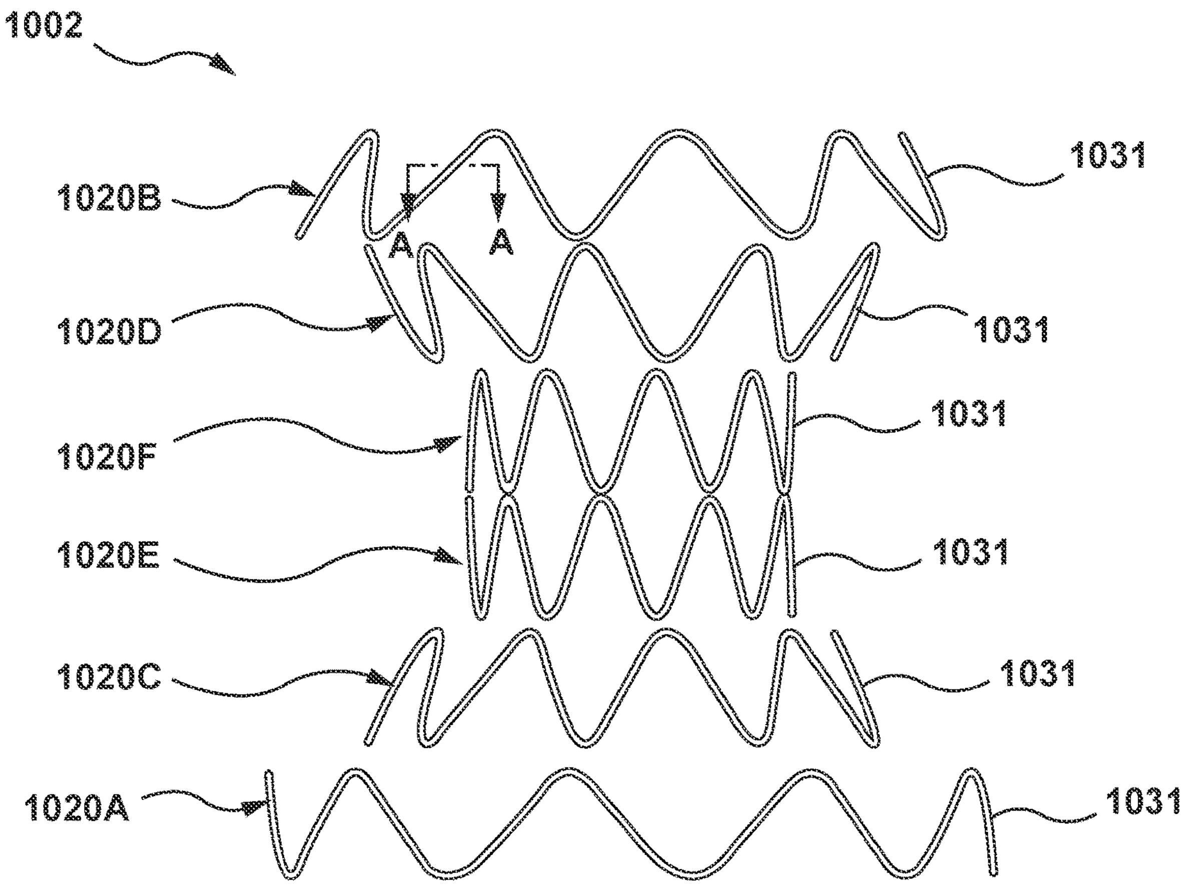
FIG. 11 is a side exploded view of a plurality of stents of the prosthetic valve device of FIG. 10A or FIG. 10B.

Another embodiment hereof is depicted in FIG. 10 and FIG. 11, in which each of the first and second longitudinal portions of the prosthetic valve device has an inductor coupled thereto such that pressure measurements at the inflow and outflow ends of the prosthetic valve device may be monitored, thereby enabling gradient (i.e., blood flow rate) calculations. More particularly, FIG. 10 depicts a prosthetic valve device 1000 with a frame 1002 extending between an inflow end 1004 of the prosthetic valve device 1000 and an outflow end 1006 of the prosthesis. The frame 1002 includes a plurality of rows 1020A, 1020B, 1020C, 1020D, 1020E, 1020F. FIG. 11 depicts an exploded view of the rows 1020A, 1020B, 1020C, 1020D, 1020E, 1020F.

Figure 11A:
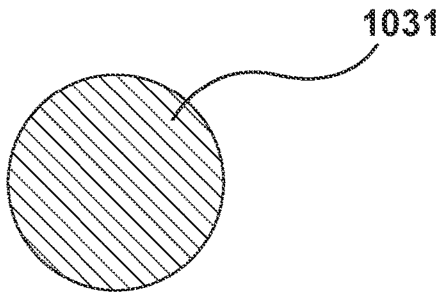
FIG. 11A is a cross-sectional view taken along line A-A of FIG. 11.

Each row 1020A, 1020B, 1020C, 1020D, 1020E, 1020F is formed from an individual or separate stent. Each stent forming one of the rows 1020A, 1020B, 1020C, 1020D, 1020E, 1020F is manufactured or formed in its radially expanded or deployed configuration and is constructed from a solid wire 1031 that is shaped into a sinusoidal patterned ring. Each row 1020A, 1020B, 1020C, 1020D, 1020E, 1020F is formed from the wire 1031 of a relatively strong, self-expanding material. In an embodiment, each row 1020A, 1020B, 1020C, 1020D, 1020E, 1020F is constructed from a self-expanding or spring material, including but not limited to nickel titanium alloys such as Nitinol™. FIG. 11A illustrates a cross-sectional view taken along line A-A of FIG. 11, through the stent forming the outflow row 1020B. As shown, the wire 1031 may have a circular cross-section.

The prosthetic valve device 1000 includes a first sensor 1040A, which is the same as the sensor 140, 240 described above, and a first inductor 1038A. The first sensor 1040A is shown attached to a strut of the second body row 1020D, but this placement is exemplary. The first sensor 1040A may be attached to any portion of the frame 1002 and/or the tubular graft 1010.

Rather than being formed by a portion of the frame 1002, the first inductor 1038A is a coil having a plurality of windings coupled to the frame 1002. A first end of the coil/first inductor 1038A is attached to a first end 1041A of the first sensor 1040A and a second end of the coil/first inductor 1038A is attached to a second end 1041B of the first sensor 1040A. The first inductor 1038A is in electrical communication with the first sensor 1040A and is configured to relay or output a signal or frequency, which is associated with the first sensor 1040A, to be received by an external detector. In the depicted embodiment, the first inductor 1038A encircles and is coupled to the second body row 1020D of the frame 1002 but may additionally and/or alternatively encircle the outflow row 1020B and/or the fourth body row 1020F. In an embodiment, the first conductor 1038A is woven or braided through a tubular graft 1010 of the prosthetic valve device 1000 in order to be coupled thereto. More particularly, a flexible strand of electrically conductive material may be woven into the material of the tubular graft 1010 in a coil shape or pattern to form the first inductor 1038A. In an embodiment, the strand of electrically conductive material may be stainless steel coated with a polymer such as Paralyne for insulation. In another embodiment, the strand of electrically conductive material may be platinum, copper, gold, nickel, aluminum, silver, and the like. Further, as an alternative to being woven into the tubular graft 1010, the first inductor 1038A may be secured to the tubular graft 1010 and/or the stent forming one of the rows 1020B, 1020D, 1020F via sutures, adhesive, and the like.

The first inductor 1038A generates an inductance L, or a change in electrical current therein. When the first sensor 1040A experiences an increase or decrease in capacitance due to forces applied against the diaphragm as previously described herein with respect to the sensor 140, 240, the frequency of the integrated circuit changes, which in turn generates the inductance L of the first inductor 1038A resulting in an output of the signal or frequency. The signal or frequency relayed or output by the first inductor 1038A is intercepted, detected, or otherwise received by the external detector. The signal or frequency of the first inductor 1038A is transmitted to the external detector through inductive coupling, such that the signal emitted from the first inductor 1038A creates interference or inductance with the external detector.

The prosthetic valve device 1000 also includes a second sensor 1040B, which is the same as the sensor 140, 240 described above, and a second inductor 1038B. The second sensor 1040B is shown attached to a strut of the first body row 1020C, but this placement is exemplary. The second sensor 1040B may be attached to any portion of the frame 1002 and/or the tubular graft 1010.

Rather than being formed by a portion of the frame 1002, the second inductor 1038B is a coil having a plurality of windings coupled to the frame 1002. A first end of the coil/second inductor 1038B is attached to a first end 1041C of the second sensor 1040B and a second end of the coil/second inductor 1038B is attached to a second end 1041D of the second sensor 1040B. The second inductor 1038B is in electrical communication with the second sensor 1040B and is configured to relay or output a signal or frequency, which is associated with the sensor 1040B, to be received by an external detector. In the depicted embodiment, the second inductor 1038B encircles and is coupled to the first body row 1020C of the frame 1002 but may additionally and/or alternatively encircle the inflow row 1020A and/or the third body row 1020E. In an embodiment, the second conductor 1038B is woven or braided through the tubular graft 1010 of the prosthetic valve device 1000 in order to be coupled thereto. More particularly, a flexible strand of electrically conductive material may be woven into the material of the tubular graft 1010 in a coil shape or pattern to form the second inductor 1038B. In an embodiment, the strand of electrically conductive material may be stainless steel coated with a polymer such as Paralyne for insulation. In another embodiment, the strand of electrically conductive material may be platinum, copper, gold, nickel, aluminum, silver, and the like. Further, as an alternative to being woven into the tubular graft 1010, the second inductor 1038 may be secured to the tubular graft 1038 and/or the stent forming one of the rows 1020A, 1020C, 1020E via sutures, adhesive, and the like.

The second inductor 1038B generates an inductance L, or a change in electrical current therein. When the second sensor 1040 experiences an increase or decrease in capacitance due to forces applied against the diaphragm as previously described herein with respect to the sensor 140, 240, the frequency of the integrated circuit changes, which in turn generates the inductance L of the second inductor 1038B resulting in an output of the signal or frequency. The signal or frequency relayed or output by the second inductor 1038B is intercepted, detected, or otherwise received by the external detector. The signal or frequency of the second inductor 1038B is transmitted to the external detector through inductive coupling, such that the signal emitted from the second inductor 1038B creates interference or inductance with the external detector.

The prosthetic valve device 1000 thus includes the second sensor 1040B, in electrical communication with the second inductor 1038B, disposed at the inflow end 1004 of the prosthetic valve device 1000 and the first sensor 1040A, in electrical communication with the first inductor 1038A, disposed at the outflow end 1006 of the prosthetic valve device 1000. Stated another way, the second sensor 1040B is disposed closer to the inflow end 1004 of the prosthetic valve device 1000 and the first sensor 1040A is disposed closer to the outflow end 1006 of the prosthetic valve device 1000. By arranging the first sensor 1040A and the second sensor 1040B in this manner, or in similar configurations where the first sensor 1040A and the second sensor 1040B are separated from each other by a longitudinal distance, a gradient flow parameter (i.e., blood flow rate) may be measured between the first sensor 1040A and the second sensor 1040B, or a measured increase or decrease in pressure caused by the flowing fluid. More particularly, the flow parameter measured may be a gradient indicating a rise or drop in blood pressure between certain points on the prosthetic valve device 1000 represented by the locations of the first sensor 1040A and the second sensor 1040B.

Figure 10A:
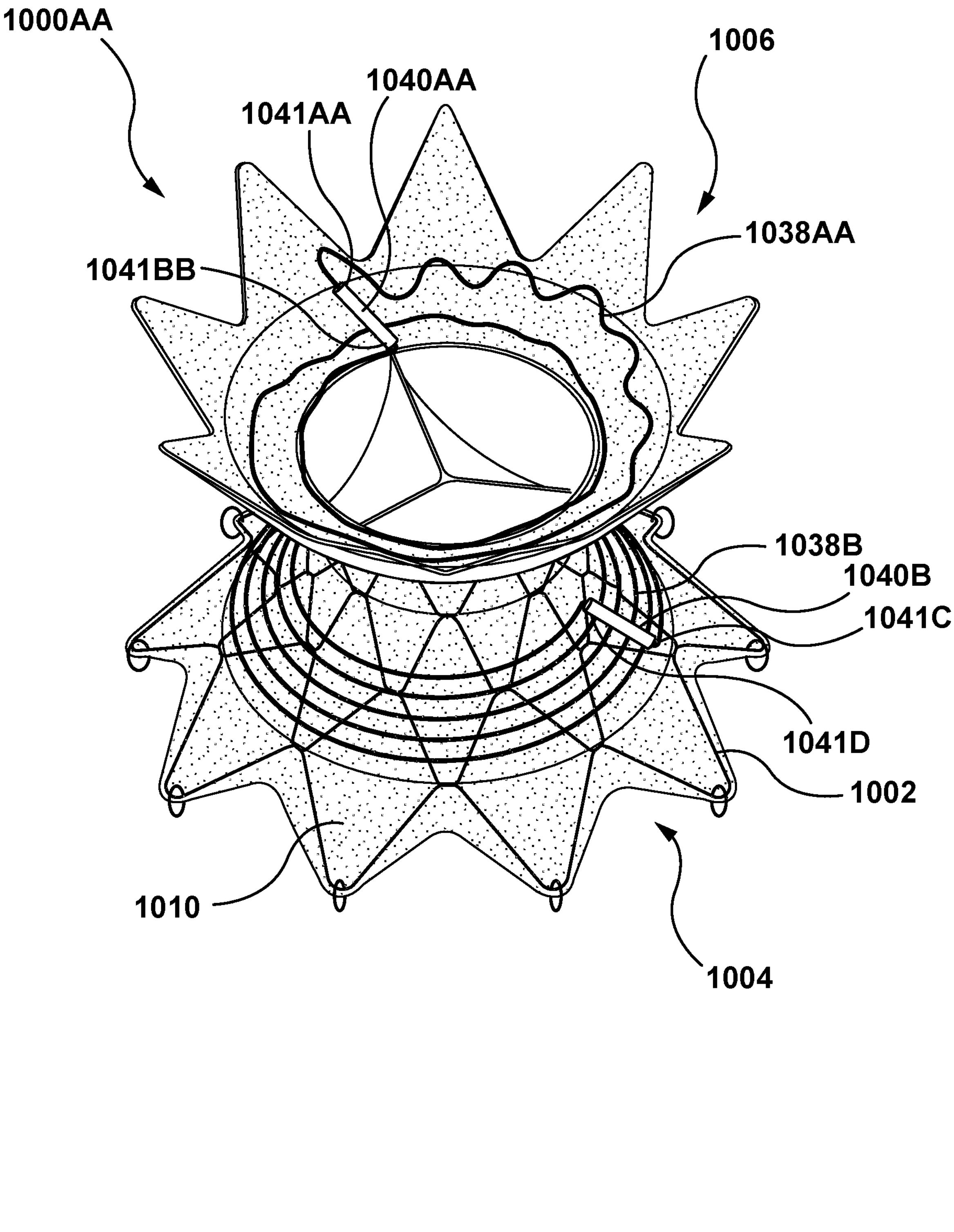
FIG. 10A is a perspective view of a prosthetic valve device according to another aspect of the present disclosure, wherein the prosthetic valve device is shown in its radially expanded or deployed configuration, and wherein the prosthetic valve device includes a first sensor in electrical communication with a first inductor coupled to the prosthetic valve device, the first inductor being a coil having a sinusoidal configuration along its length.

A variation of the prosthetic valve device 1000 is shown in FIG. 10A and labeled as prosthetic valve device 1000AA. Prosthetic valve device 1000AA is the same as prosthetic valve device 1000, except for the differences noted herein. A first inductor 1038AA of the prosthetic valve device 1000AA is a coil having a plurality of windings. The first inductor 1038AA is similar to the first inductor 1038A of the prosthetic valve device 1000, except that the first inductor 1038AA has a sinusoidal configuration along its windings or coiled length. The sinusoidal configuration is configured to further permit or encourage radial compression of the inductor 1038AA when the prosthetic valve device 1000 is radially compressed for delivery. A first end of the coil/first inductor 1038AA is attached to a first end 1041AA of a first sensor 1040AA and a second end of the coil/first inductor 1038AA is attached to a second end 1041BB of the second sensor 1040B. Although only the first inductor 1038AA is shown herein with the sinusoidal configuration, any of second inductor 938, first inductor 1038A, and second inductor 1038B may have a sinusoidal configuration along its windings or coiled length.

Turning now to the block diagram of FIG. 12, the interaction between the external device 150 and the prosthetic valve device 100/700/800/900/1000/1000A will be described in more detail. As described above, the inductor 138/738/838/938/1038A/1038B of the respective prosthetic valve device is configured to output or relay a signal 160 associated with the respective sensor(s) 140/240/740/840/940/1040A/1040B to be received by the antenna 156 of the external detector 150. In addition to the antenna 156, the external detector 150 includes a waveform generator or vector network analyzer 152 having a Graphical User Interface (GUI) 158 for displaying information (such as the measured flow parameters) to an end user. The waveform generator 152 (with an integrated GUI 158) may be a commercially available waveform generator available from Keysight of Santa Rosa, CA. Alternatively, the GUI 158 may be separate from but connected to the external detector 150 by wireless means such as cellular, bluetooth, WiFi, and the like. For example, as shown in FIG. 13, the data received from the external detector 150 may further be transmitted to an end user's device 159 for display. The end user's device 159 may be, for example, a cell phone, laptop, or desktop computer. In embodiments, the external detector 150 may be provided with a strap or band 154, or other suitable means, for securing the external detector 150 against the body of the end user, as illustrated in FIG. 13. Alternatively, the external detector 150 may be placed anywhere within the vicinity of the end user to properly receive the frequency or signal 160 emitted from the inductor 138/738/838/938/1038A/1038B. In an embodiment, the external detector 150 is configured to communicate with the inductor 138/738/838/938/1038A/1038B by being placed in the vicinity of the sensor(s) 140/240/740/840/940/1040A/1040B and is also configured to power or charge the sensor(s) 140/240/740/840/940/1040A/1040B, as represented by directional arrow 162 on FIG. 12.

Figure 12:
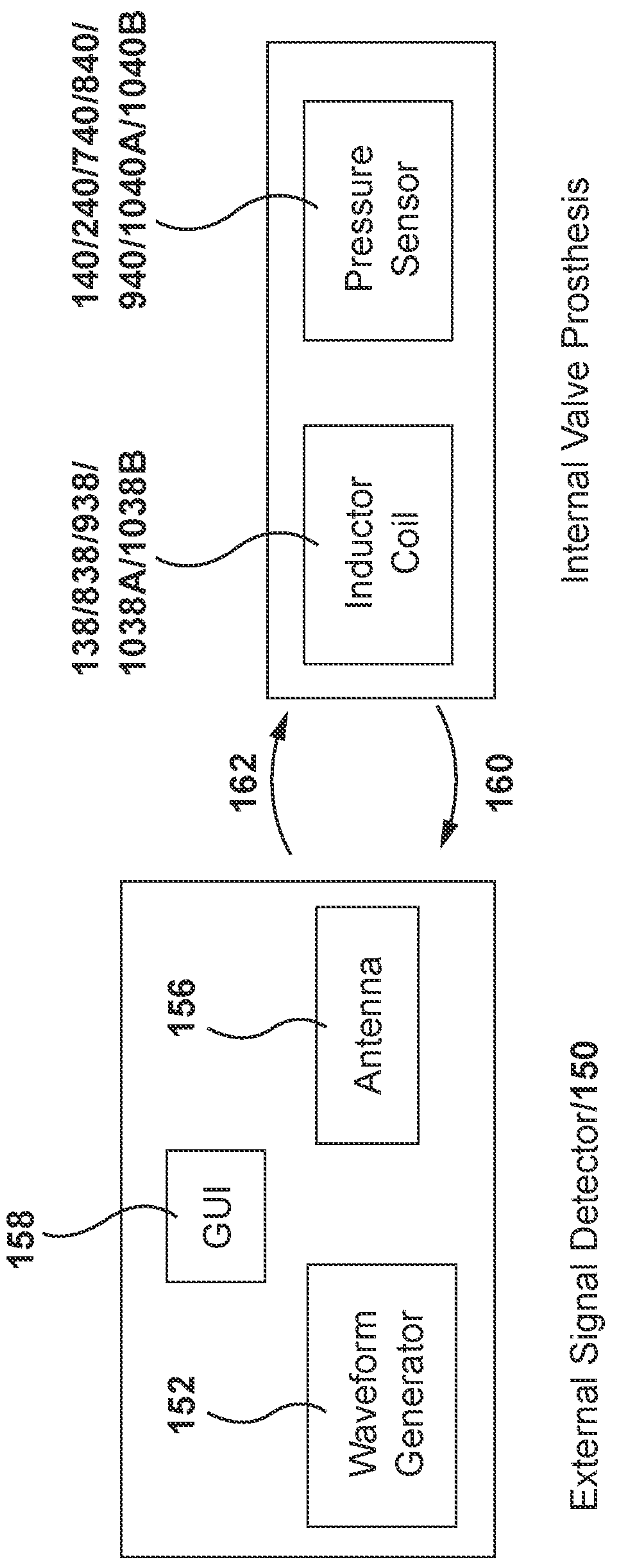
FIG. 12 is a schematic of a prosthetic valve device of any embodiment hereof in communication with an external detector.
Figure 13:
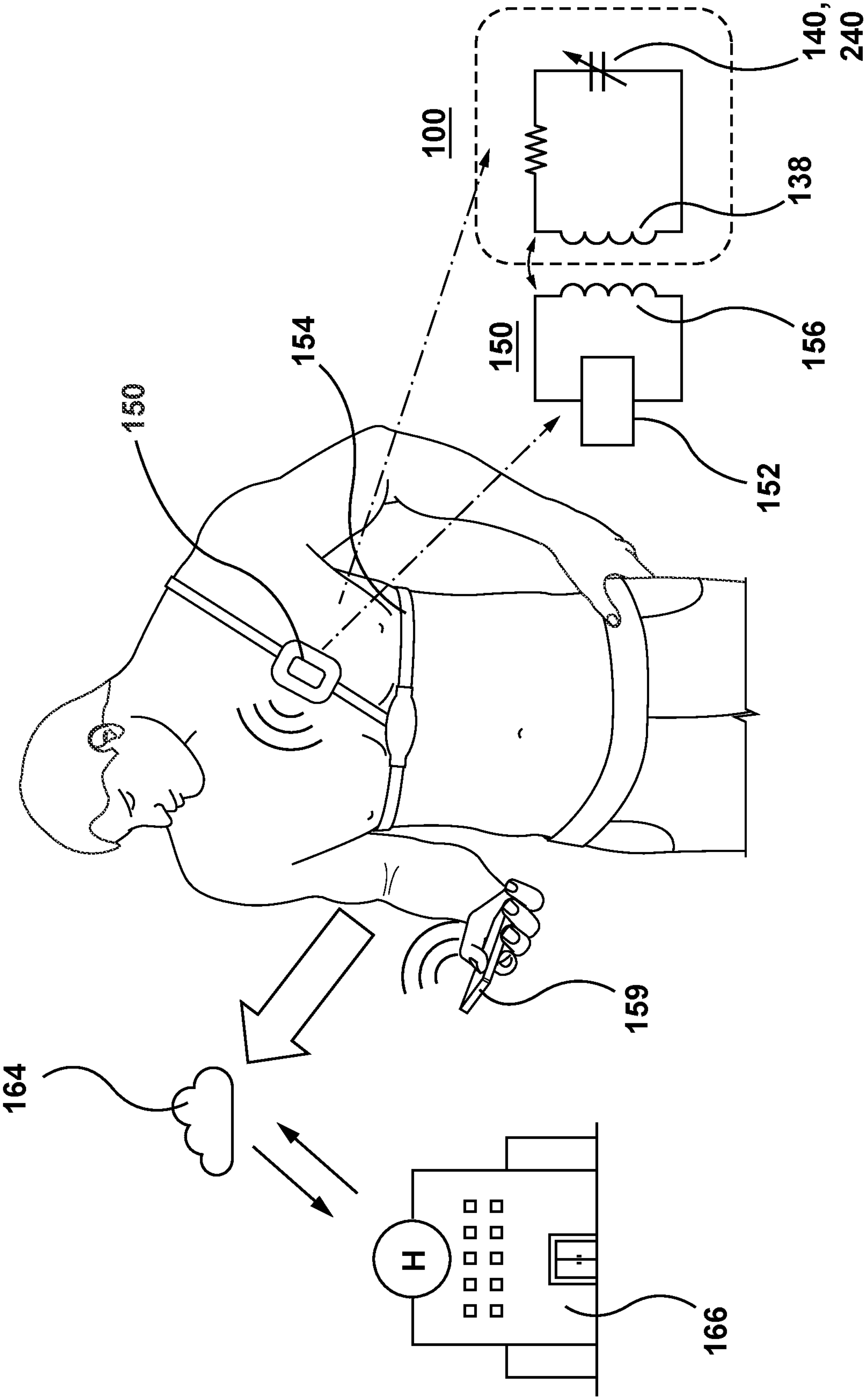
FIG. 13 is a schematic diagram of an end user interacting with the external detector of FIG. 12.

With reference to FIGS. 12 and 13, and as previously described with reference to FIG. 6E, the external detector 150 may also perform as a powering device for supplying power transfer to the circuitry including the sensor(s) 140/240/740/840/940/1040A/1040B and inductor 138/738/838/938/1038A/1038B as described herein. More particularly, the patient may hold the external device 150 at a specific location and/or in a specific orientation close to the sensor(s) 140/240/740/840/940/1040A/1040B, i.e., on the chest. Once in place, powering on the waveform generator 152 will initiate inductive coupling from the antenna 156 to the inductor 138 and generate an alternating current (AC power) within the circuitry including the sensor(s) 140/240/740/840/940/1040A/1040B. This AC power supplied to the circuitry including the sensor(s) 140/240/740/840/940/1040A/1040B allows for the transmission of the signal 160 from the inductor 138 back to the antenna 156, which is then processed and the resonance frequency is measured by the waveform generator 152.

With further reference to FIG. 13, post implantation, the patient may wear or hold the external device 150 for a time sufficient for signal reception, i.e., 10-20 minutes. Once the signal 160 is received by the external device 150, the signal 160 may be processed in the cloud 164. Processing of the signal 160 may include sensor data calibration, data processing, and recording/outputting of the flow parameter. The flow parameter may then be transmitted to the end user's device 159 for display, as previously mentioned, and also may be transmitted to the patient's physician, represented by building 166. Since the flow parameter is made available to the patient's physician upon processing, the physician may review the data and promptly identify any issues with prosthetic valve device 100 needing further treatment.

Figure 14:
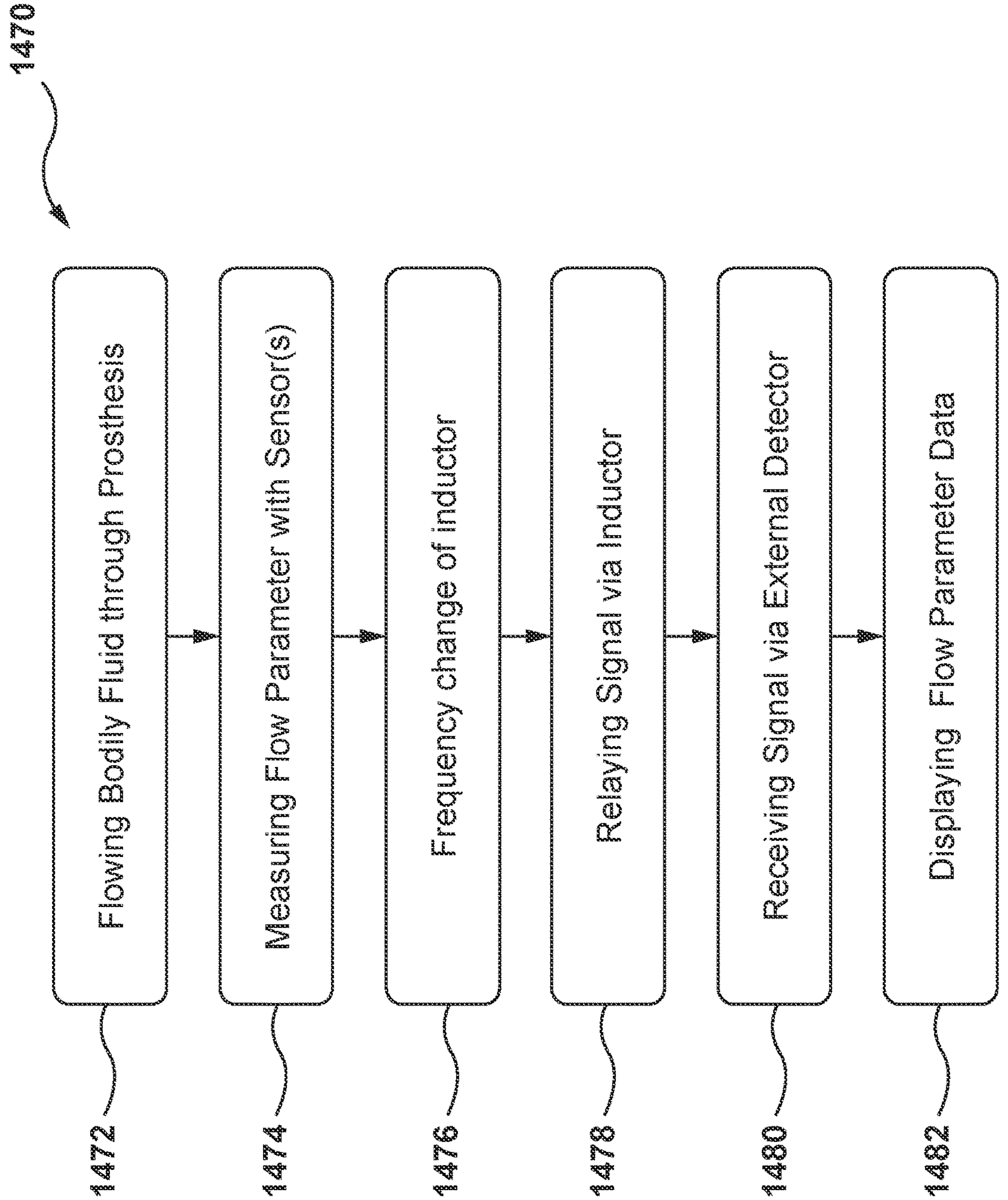
FIG. 14 is a flowchart illustrating a method of measuring a flow parameter using a prosthetic valve device of any embodiment hereof.

Further provided is a method 1470 for measuring a flow parameter within the prosthesis or valve device 100 implanted within a body as described herein, the method as illustrated in FIG. 14. In operation 1472, a bodily fluid flows through the inflow end 112 of the tubular graft 110 of the device 100, through the prosthetic valve component 108, to the outflow end 114 of the tubular graft 110. In operation 1474, the at least one sensor 140, 240 disposed on or within the prosthetic valve device 100 as described herein measures the flow parameter of the bodily fluid determined by the forces generated from the bodily fluid against the diaphragm 142 of the at least one sensor 140, 240 as previously described herein. In operation 1476, this measured flow parameter is then electrically communicated to the inductor 138, and in operation 1478, the inductor 138 relays the signal 160 to be received by the external detector 150. More particularly, the signal 160 relays information pertaining to pressure measured by the at least one sensor 140, 240. In embodiments, the external detector 150 is held in place against an external surface of a body of the end user, i.e., on the chest or back near the heart, using means of securing as previously described above. Holding the external detector 150 against the end user may further result in the external detector 150 charging/powering the at least one sensor 140, 240, thus allowing for the sensor 140, 240 to measure the flow parameter for transmission via the inductor 138 by the signal 160. In operation 1480, the external detector 150 receives the signal 160, and in operation 1482, the external detector 150 may then display the measured flow parameter on a display or GUI 158 integral with or connected to (either via wireless or hard-wired connection) to external detector 150. In embodiments where two or more sensors separated by a longitudinal distance therebetween are connected to the valve device 100, a first flow parameter at the inflow end 112 is measured via the first sensor, and a second flow parameter at the outflow end 114 is measured via the second sensor, as the bodily fluid flows through the device 100. By using multiple sensors separated by a longitudinal distance therebetween, the first flow parameter and the second flow parameter may be used in determining a gradient flow parameter (i.e., blood flow rate) for communication to and display by the external detector 150.

Although the sensors and inductors described herein are incorporated onto self-expanding prosthetic valve devices, such sensors and inductors may alternatively be incorporated onto balloon-expandable or mechanically expandable prosthetic valve devices. As such, the frame would alternatively be made from a plastically deformable material such that when expanded, the frame maintains its radially expanded configuration. Suitable plastically deformable materials include cobalt chromium alloys such as MP35N, which would be utilized in place of Nitinol is the self-expandable embodiments described herein.

The foregoing description has been presented for purposes of illustration and enablement and is not intended to be exhaustive or to limit the invention to the precise form disclosed. Other modifications and variations are possible in light of the above teachings. The embodiments and examples were chosen and described in order to best explain the principles of the invention and its practical application and to thereby enable others skilled in the art to best utilize the invention in various embodiments and various modifications as are suited to the particular use contemplated. It is intended that the appended claims be construed to include other alternative embodiments of the invention.

Embodiments of the present disclosure include the following examples.

In a first example, a prosthesis for implantation within a body or lumen includes a frame including a plurality of rows of struts and crowns formed between adjacent pairs of said struts. Each row has a first set of crowns and a second set of crowns with the first set of crowns being disposed closer to an inflow end of the prosthesis than the second set of crowns, the frame having a first longitudinal portion and a second longitudinal portion disposed axially adjacent to the first longitudinal portion. The second longitudinal portion forms at least two rows of the plurality of rows and the first longitudinal portion forms at least two rows of the plurality of rows. The second longitudinal portion is formed from a single composite wire having a first end and a second end opposing the first end. The composite wire has a core of a first material, an intermediate layer of a second material, and an outer layer of a third material. The third material is an electrically insulative material. A prosthetic valve component is disposed within the frame. At least one sensor is configured to measure a flow parameter within the prosthesis. A first end of the sensor is attached to the first end of the single component wire and a second end of the sensor is attached to the second end of the single composite wire. The second longitudinal portion forms an inductor configured to relay a signal to an external detector, the signal being associated with the at least one sensor.

In a second example, in the prosthesis according to any of the previous or subsequent examples herein, the first longitudinal portion forms three rows of the plurality of rows and the second longitudinal portion forms three rows of the plurality of rows.

In a third example, in the prosthesis according to any of the previous or subsequent examples herein, a length of the first longitudinal portion is substantially equal to a length of the second longitudinal portion.

In a fourth example, in the prosthesis according to any of the previous or subsequent examples herein, the second set of crowns of each row is disposed against and attached to the first set of crowns of an adjacent row by at least two axial suture loops extending over adjacent crowns.

In a fifth example, in the prosthesis according to any of the previous or subsequent examples herein, the first longitudinal portion includes an inflow end of the prosthesis and the second longitudinal portion includes an outflow end of the prosthesis.

In a sixth example, in the prosthesis according to any of the previous or subsequent examples herein, the first longitudinal portion is stronger than the second longitudinal portion.

In a seventh example, in the prosthesis according to any of the previous or subsequent examples herein, the first longitudinal portion includes an inflow stent disposed at the inflow end of the prosthesis and at least one body stent disposed between the second longitudinal portion and the inflow stent, each of the inflow stent and the at least one body stent being a sinusoidal patterned radially expandable ring that forms one row of the plurality of rows.

In an eighth example, in the prosthesis according to any of the previous or subsequent examples herein, each sinusoidal patterned radially expandable ring is composed of nitinol wire.

In a nineth example, in the prosthesis according to any of the previous or subsequent examples herein, the prosthetic valve component is disposed adjacent to a junction between the first longitudinal portion and the second longitudinal portion.

In a tenth example, in the prosthesis according to any of the previous or subsequent examples herein, the first longitudinal portion of the frame is formed from one or more solid wires of the second material.

In an eleventh example, in the prosthesis according to any of the previous or subsequent examples herein, the first material is platinum and the second material is nitinol.

In a twelfth example, in the prosthesis according to any of the previous or subsequent examples herein, the at least one sensor is a passive capacitive pressure sensor.

In a thirteenth example, in the prosthesis according to any of the previous or subsequent examples herein, the flow parameter is blood pressure.

In a fourteenth example, in the prosthesis according to any of the previous or subsequent examples herein, the at least one sensor includes a first sensor and the prosthesis further includes a second sensor. The flow parameter is a gradient between the first sensor and the second sensor.

In a fifteenth example, in the prosthesis according to any of the previous or subsequent examples herein, the second sensor is disposed closer to an inflow end of the prosthesis and the first sensor is disposed closer to an outflow end of the prosthesis.

In a sixteenth example, in the prosthesis according to any of the previous or subsequent examples herein, the at least one sensor is a compliant sensor or a rigid sensor.

In a seventeenth example, in the prosthesis according to any of the previous or subsequent examples herein, the at least one sensor includes a plurality of sensors and each sensor of the plurality of sensors is electrically coupled to the second longitudinal portion of the frame.

In an eighteenth example, in the prosthesis according to any of the previous or subsequent examples herein, the at least one sensor is wireless and batteryless.

In a nineteenth example, in the prosthesis according to any of the previous or subsequent examples herein, the external detector is configured to power the at least one sensor and communicate with the inductor.

In a twentieth example, in the prosthesis according to any of the previous or subsequent examples herein, the signal relayed by the inductor to the external detector is achieved through inductive coupling.

In a twenty-first example, in the prosthesis according to any of the previous or subsequent examples herein, the inductor is a first inductor and the at least one sensor is a first sensor. The first longitudinal portion is formed from a second single composite wire having a first end and a second end opposing the first end, the composite wire having a core of the first material, an intermediate layer of the second material, and an outer layer of the third material. The prosthesis further includes a second sensor electrically coupled to the first longitudinal portion of the frame, the second sensor being configured to measure the flow parameter within the prosthesis. A first end of the second sensor is attached to the first end of the second single component wire and a second end of the second sensor is attached to the second end of the second single composite wire. The first longitudinal portion forms a second inductor configured to relay a signal to the external detector, the signal being associated with the second sensor.

In a twenty-second example, in the prosthesis according to any of the previous or subsequent examples herein, the inductor is a first inductor and the at least one sensor is a first sensor. The prosthesis further includes a second sensor electrically coupled to the first longitudinal portion of the frame, the second sensor being configured to measure the flow parameter within the prosthesis. The prosthesis further includes a coil having a plurality of windings coupled to the first longitudinal portion of the frame and electrically coupled to the second sensor, the coil forming a second inductor configured to relay a signal to the external detector, the signal being associated with the second sensor.

In a twenty-third example, in the prosthesis according to any of the previous or subsequent examples herein, the coil is formed from stainless steel coated with a polymer.

In a twenty-fourth example, in the prosthesis according to any of the previous or subsequent examples herein, the coil has a sinusoidal configuration along its length.

In a twenty-fifth example, a prosthesis for implantation within a body or lumen includes a tubular graft defining a lumen that extends from an inflow end to an outflow end. A prosthetic valve component is disposed within the lumen of the tubular graft. A frame is attached to the tubular graft, the frame including an inflow stent attached to the inflow end of the tubular graft, an outflow stent attached to the outflow end of the tubular graft, and a plurality of body stents attached to the tubular graft and disposed between the inflow stent and the outflow stent. Each stent of the plurality of body stents, the inflow stent, and the outflow stent is a sinusoidal patterned radially expandable ring having a first set of crowns and a second set of crowns. The prosthesis also includes a coil having a plurality of windings. The coil is woven into the tubular graft to encircle a portion of the frame. At least one sensor is electrically coupled to the coil, the at least one sensor being configured to measure a flow parameter within the prosthesis. The coil forms an inductor configured to relay a signal to an external detector, the signal being associated with the at least one sensor.

In a twenty-sixth example, in the prosthesis according to any of the previous or subsequent examples herein, a first body stent of the plurality of body stents is disposed directly adjacent to the inflow stent and a second body stent of the plurality of body stents is disposed directly adjacent to the outflow stent. Each of the inflow stent, the outflow stent, and each stent of the plurality of body stents is a sinusoidal patterned radially expandable ring having a first set of crowns and a second set of crowns.

In a twenty-seventh example, in the prosthesis according to any of the previous or subsequent examples herein, each of the inflow stent, the outflow stent, and the plurality of body stents are composed of nitinol wire.

In a twenty-eighth example, in the prosthesis according to any of the previous or subsequent examples herein, the coil is formed from stainless steel coated with a polymer.

In a twenty-ninth example, in the prosthesis according to any of the previous or subsequent examples herein, the coil has a sinusoidal configuration along its length.

In a thirtieth example, in the prosthesis according to any of the previous or subsequent examples herein, the second set of crowns of each stent is disposed against and attached to the first set of crowns of an adjacent stent by at least two axial suture loops extending over adjacent crowns.

In a thirty-first example, in the prosthesis according to any of the previous or subsequent examples herein, the at least one sensor is a passive capacitive pressure sensor.

In a thirty-second example, in the prosthesis according to any of the previous or subsequent examples herein, the flow parameter is blood pressure.

In a thirty-third example, in the prosthesis according to any of the previous or subsequent examples herein, the at least one sensor includes a first sensor and the prosthesis further includes a second sensor. The flow parameter is a gradient between the first sensor and the second sensor.

In a thirty-fourth example, in the prosthesis according to any of the previous or subsequent examples herein, the second sensor is disposed closer to an inflow end of the prosthesis and the first sensor is disposed closer to an outflow end of the prosthesis.

In a thirty-fifth example, in the prosthesis according to any of the previous or subsequent examples herein, the at least one sensor is a compliant sensor or a rigid sensor.

In a thirty-sixth example, in the prosthesis according to any of the previous or subsequent examples herein, the at least one sensor includes a plurality of sensors, and each sensor of the plurality of sensors is electrically coupled to the coil.

In a thirty-seventh example, in the prosthesis according to any of the previous or subsequent examples herein, the at least one sensor is wireless and batteryless.

In a thirty-eighth example, in the prosthesis according to any of the previous or subsequent examples herein, the external detector is configured to power the at least one sensor and communicate with the inductor.

In a thirty-ninth example, in the prosthesis according to any of the previous or subsequent examples herein, the signal relayed by the inductor to the external detector is achieved through inductive coupling.

In a fortieth example, a method for measuring a flow parameter within a prosthesis of any of the preceding claims implanted within a lumen of a body includes measuring the flow parameter with at least one sensor. The flow parameter is communicated to the inductor in electrical communication with the at least one sensor. A signal associated with the at least one sensor is relayed via the inductor. The signal is received via an antenna of the external detector. The flow parameter measured by the at least one sensor is displayed on a display integral or connected to the external detector.

In a forty-first example, in the method according to any of the previous or subsequent examples herein, the flow parameter is blood pressure.

In a forty-second example, in the method according to any of the previous or subsequent examples herein, the flow parameter is a blood flow rate.

In a forty-third example, in the method according to any of the previous or subsequent examples herein, the method also includes the step of holding the external detector against an external surface of a patient having the prosthetic valve device implanted therein.

In a forty-fourth example, in the method according to any of the previous or subsequent examples herein, upon holding the external detector in place against the external surface, the external detector powers the at least one sensor.

In a forty-fifth example, in the method according to any of the previous or subsequent examples herein, the step of relaying the signal is achieved through inductive coupling between the inductor of the prosthetic valve and the antenna of the external device.

What is claimed is:

1. A prosthesis for implantation within a body or lumen, comprising:

a frame including a plurality of rows of struts and crowns formed between adjacent pairs of said struts, each row having a first set of crowns and a second set of crowns with the first set of crowns being disposed closer to an inflow end of the prosthesis than the second set of crowns, the frame having a first longitudinal portion and a second longitudinal portion disposed axially adjacent to the first longitudinal portion, wherein the second longitudinal portion forms at least two rows of the plurality of rows and the first longitudinal portion forms at least two rows of the plurality of rows, and wherein the second longitudinal portion is formed from a single composite wire having a first end and a second end opposing the first end, the composite wire having a core of a first material, an intermediate layer of a second material, and an outer layer of a third material, the third material being an electrically insulative material;

a prosthetic valve component disposed within the frame;

at least one sensor configured to measure a flow parameter within the prosthesis, wherein a first end of the sensor is attached to the first end of the single composite wire and a second end of the sensor is attached to the second end of the single composite wire; and wherein the second longitudinal portion forms an inductor configured to relay a signal to an external detector, the signal being associated with the at least one sensor.

2. The prosthesis of claim 1, wherein the first longitudinal portion forms three rows of the plurality of rows and the second longitudinal portion forms three rows of the plurality of rows.

3. The prosthesis of claim 1, wherein the plurality of rows include an inflow row, an outflow row, and a plurality of body rows disposed between the outflow row and the inflow row, and wherein the second set of crowns of each body row and the inflow row is disposed against and attached to the first set of crowns of an adjacent row by at least two axial suture loops extending over adjacent crowns.

4. The prosthesis of claim 1, wherein the first longitudinal portion includes an inflow end of the prosthesis and the second longitudinal portion includes an outflow end of the prosthesis.

5. The prosthesis of claim 1, wherein the prosthetic valve component is disposed adjacent to a junction between the first longitudinal portion and the second longitudinal portion.

6. The prosthesis of claim 1, wherein the first longitudinal portion of the frame is formed from one or more solid wires of the second material.

7. The prosthesis of claim 1, wherein the first material is platinum and the second material is nitinol.

8. The prosthesis of claim 1, wherein the at least one sensor is a passive capacitive pressure sensor.

9. The prosthesis of claim 8, wherein the flow parameter is blood pressure.

10. The prosthesis of claim 1, wherein the at least one sensor includes a first sensor and the prosthesis further includes a second sensor, and wherein the flow parameter is a gradient between the first sensor and the second sensor.

11. The prosthesis of claim 10, wherein the second sensor is disposed closer to an inflow end of the prosthesis and the first sensor is disposed closer to an outflow end of the prosthesis.

12. The prosthesis of claim 1, wherein the at least one sensor is a compliant sensor or a rigid sensor.

13. The prosthesis of claim 1, wherein the at least one sensor includes a plurality of sensors, and wherein each sensor of the plurality of sensors is electrically coupled to the second longitudinal portion of the frame.

14. The prosthesis of claim 1, wherein the at least one sensor is wireless and batteryless.

15. The prosthesis of claim 1, wherein the external detector is configured to power the at least one sensor and communicate with the inductor.

16. The prosthesis of claim 1, wherein the signal relayed by the inductor to the external detector is achieved through inductive coupling.

17. The prosthesis of claim 1, wherein the inductor is a first inductor and the at least one sensor is a first sensor, and wherein the first longitudinal portion is formed from a second single composite wire having a first end and a second end opposing the first end, the composite wire having a core of the first material, an intermediate layer of the second material, and an outer layer of the third material, and wherein the prosthesis further includes a second sensor electrically coupled to the first longitudinal portion of the frame, the second sensor being configured to measure the flow parameter within the prosthesis, wherein a first end of the second sensor is attached to the first end of the second single composite wire and a second end of the second sensor is attached to the second end of the second single composite wire, and wherein the first longitudinal portion forms a second inductor configured to relay a signal to the external detector, the signal being associated with the second sensor.

18. The prosthesis of claim 1, wherein the inductor is a first inductor and the at least one sensor is a first sensor, and wherein the prosthesis further includes a second sensor electrically coupled to the first longitudinal portion of the frame, the second sensor being configured to measure the flow parameter within the prosthesis, and wherein the prosthesis further includes a coil having a plurality of windings coupled to the first longitudinal portion of the frame and electrically coupled to the second sensor, the coil forming a second inductor configured to relay a signal to the external detector, the signal being associated with the second sensor.

19. The prosthesis of claim 18, wherein the coil is formed from stainless steel coated with a polymer.

20. The prosthesis of claim 19, wherein the coil has a sinusoidal configuration along its length.

* * * * *